(12) United States Patent
Lötvall et al.

(10) Patent No.: US 9,856,477 B2
(45) Date of Patent: Jan. 2, 2018

(54) DELIVERY OF THERAPEUTIC AGENT

(71) Applicant: Codiak BioSciences, Inc., Woburn, MA (US)

(72) Inventors: Jan Lötvall, Mölnlycke (SE); Jonas Andrej Nilsson, Kållered (SE)

(73) Assignee: Codiak BioSciences, Inc., Cambridge, MA (US)

(*) Notice: Subject to any disclaimer, the term of this patent is extended or adjusted under 35 U.S.C. 154(b) by 0 days.

(21) Appl. No.: 14/442,578

(22) PCT Filed: Nov. 13, 2013

(86) PCT No.: PCT/EP2013/073740
§ 371 (c)(1),
(2) Date: May 13, 2015

(87) PCT Pub. No.: WO2014/076137
PCT Pub. Date: May 22, 2014

(65) Prior Publication Data
US 2016/0168572 A1 Jun. 16, 2016

(30) Foreign Application Priority Data
Nov. 13, 2012 (SE) .................................. 1251290

(51) Int. Cl.
*A61K 48/00* (2006.01)
*C12N 15/113* (2010.01)
*C12N 15/11* (2006.01)
*C12N 15/85* (2006.01)

(52) U.S. Cl.
CPC ........ *C12N 15/1135* (2013.01); *C12N 15/111* (2013.01); *C12N 15/85* (2013.01); *C12N 2310/14* (2013.01); *C12N 2320/30* (2013.01); *C12N 2320/32* (2013.01)

(58) Field of Classification Search
CPC ...................................................... C07H 21/04
See application file for complete search history.

(56) References Cited

U.S. PATENT DOCUMENTS 7,056,704 B2 * 6/2006 Tuschl ................... A61K 48/00
435/6.11
7,659,389 B2 * 2/2010 McSwiggen ..... C12Y 103/0102
536/23.1
2004/0224893 A1 * 11/2004 Wang .................. A61K 38/1793
424/158.1
2013/0209544 A1 * 8/2013 Zhang ................... C12N 15/111
424/450
2015/0079631 A1 * 3/2015 Breakefield ........ A61K 31/7105
435/69.1

FOREIGN PATENT DOCUMENTS

| CN | 101869715 A | 10/2010 |
|---|---|---|
| EP | 2578236 A1 | 4/2013 |
| WO | WO-2011/147175 A1 | 12/2011 |

OTHER PUBLICATIONS

McMahon al. (Nano Lett., 2011, 11 (3), pp. 1208-1214Publication Date (Web): Feb. 14, 2011).*
Ohno et al. (Molecular Therapy Vo. 21, online publication Oct. 2012).*
Vita et al. (Seminars in Cancer Biology 2006: 318-330).*
Vickers et al. (The Journal of Biological Chemistry, vol. 278, No. 9, 2003, pp. 7108-7118).*
International Preliminary Report on Patentability dated May 28, 2015 issued in PCT Patent Application No. PCT/EP2013/073740.
International Search Report and Written Opinion dated Apr. 24, 2014 issued in PCT Patent Application No. PCT/EP2013/073740.
Lee, Y., et al. (2012), "Exosomes and microvesicles: extracellular vesicles for genetic information transfer and gene therapy", *Human Molecular Genetics*, 21(Review Issue 1): R125-R134.
Ohshima, K., et al. (2010), "Let-7 MircoRNA Family Is Selectively Secreted into the Extracellular Environment via Exosomes in a Metastatic Gastric Cancer Cell Line", *PLoS ONE*, 5(10): e13247.
Wahlgren, J., et al. (2012), "Plasma exosomes can deliver exogenous short interfering RNA to monocytes and lymphocytes", *Nucleic Acids Research*, 40(17), e130.
Wang, H., et al. (2008), "c-Myc depletion inhibits proliferation of human tumor cells at various stages of the cell cycle", *Oncogene*, 27(13): 1905-1915.
Yang, Y., et al. (2012), "Systemic Delivery of siRNA via LCP Nanoparticle Efficiently Inhibits Lung Metastasis", *Molecular Therapy*, 20(3): 609-615.
Chinese First Office Action, Chinese Application No. 201380069683.X, dated Oct. 10, 2016, 12 pages (with concise explanation of relevance).
European Examination Report, European Application No. 13789802.9, dated Sep. 23, 2016, 5 pages.
Lee, Y. et al., "Exosomes and Microvesicles: Extracellular Vesicles for Genetic Information Transfer and Gene Therapy," Human Molecular Genetics, 2012, pp. R125-R134, vol. 21, Review Issue 1.

(Continued)

*Primary Examiner* — Kimberly Chong
(74) *Attorney, Agent, or Firm* — Fenwick & West LLP

(57) ABSTRACT

A method of producing nanovesicles comprising an oligonucleotide inhibitor to an oncogene or a proto-oncogene or the gene product thereof, said method comprises a) introducing a DNA sequence encoding an oligonucleotide capable of inhibiting a human oncogenic or proto-oncogenic transcription factor, into a mammalian cell; b) allowing the cell to express said inhibitor oligonucleotide; and c) obtaining nanovesicles containing said inhibitor oligonucleotide from said cell. Nanovesicles produced by the claimed method can be effectively and specifically targeted to e.g. cancer cells to deliver the inhibitor oligonucleotide.

12 Claims, No Drawings

(56) References Cited

OTHER PUBLICATIONS

Van Dommelen, S.M. et al., "Microvesicles and Exosomes: Opportunities for Cell-Derived Membrane Vesicles in Drug Delivery," Journal of Controlled Release, 2012, pp. 635-644, vol. 161.
Chinese Second Office Action, Chinese Application No. 201380069683.X, dated Aug. 18, 2017, 16 pages (with concise explanation of relevance).

* cited by examiner

DELIVERY OF THERAPEUTIC AGENT

CROSS-REFERENCE TO RELATED APPLICATIONS

This application is the National Stage of International Application No. PCT/EP2013/073740, filed Nov. 13, 2013, which is hereby incorporated in its entirety by reference and which claims the benefit of Swedish application no. 1251290-1, filed on Nov. 13, 2012, also incorporated herein by reference.

FIELD OF THE INVENTION

The present invention relates to the delivery of potentially therapeutic agents via cell-derived vesicles.

BACKGROUND OF THE INVENTION

Cancer is a leading cause of death worldwide. In 2008, various cancers accounted for 7.6 million deaths (around 13% of all deaths), according to the World Health Organization (WHO), and this number is projected to continue rising, with an estimated 13.1 million deaths worldwide in 2030 [GLOBOCAN 2008 (IARC) Section of Cancer Information (Nov. 11, 2012)].

Malignant melanoma is responsible for a majority of deaths caused by skin tumors, and is the most common malignancy in young adults. When melanoma is metastatic, prognosis is unfavorable, and the therapeutic alternatives are few. Uveal melanoma has different clinical features than skin melanomas, and often spreads primarily to liver. For uveal melanoma it has been proposed that approximately one out of two patients will develop metastases within 15 years after treatment of the primary ocular tumor. The average survival time after diagnosis of liver metastases is 8 to 10 months and the mortality rate in patients with liver metastases of uveal melanoma is 92% over two years. One treatment option is regional perfusion of the liver with hyperthermia and melphalan. This approach is however very invasive and associated with risks of surgical complications. Even though remissions are seen in most cases, survival is only marginally prolonged.

Melanoma of the skin and uveal melanoma are merely two examples of cancer, which takes the lives of millions of people each year. Treatment of cancer is therefore one of the major challenges facing modern medicine.

In general, current anti-cancer therapeutic strategies include surgery, radiotherapy, cytotoxic drugs (chemotherapy) and hormone drugs. A drawback of chemotherapeutic agents is that they are unselective and cause adverse side effects, which effectively limits dosage and hence also the therapeutic effect. There is a need for improved, more selective cancer therapies.

A rare example of a medication directly targeted to a point mutation oncogene is vemurafenib, targeting specifically the $BRAF^{V600E}$ mutation common in skin melanomas, with relatively less off-target effects compared to chemotherapy. However this treatment only prolongs life with a few months in metastatic melanoma, and only works in those melanomas that have this specific mutation. A possibility would therefore be to target the downstream signaling molecules. The downstream targets however lack enzymatic activity, and are often impossible to treat with small molecules, because of their tertiary structure. Further, as a small molecule inhibitor would distribute throughout the body, it would also cause systemic side effects in normal, healthy cells that are depending on such downstream molecules.

Over the last decade, gene therapy has received increased attention and it is believed that in the future gene therapy may be applicable to many diseases, including cancer.

The most common form of gene therapy involves using DNA that encodes a functional, therapeutic gene in order to replace a mutated gene. Other types of gene therapy involve directly correcting a mutation, or using DNA that encodes a therapeutic protein drug (rather than a natural human gene) to provide treatment. It has also been suggested that RNA interference, referred to as RNAi, may be possible to exploit in gene therapy against e.g. infections or cancer.

RNAi is a gene regulating mechanism occurring in many eukaryotic cells which has been known since the late 1990's, and which has been, used primarily as a research tool to achieve gene knockout.

However, a major challenge for the development of RNAi-based therapeutics and other gene therapy applications is delivery of the therapeutic agent (e.g. an RNA molecule). Viral vectors may be efficient, but give rise to safety concerns, and can be rapidly eliminated by a patient's immune system, reducing its impact.

The mode of delivery is particularly important when the target is a gene or gene product that is important to the function also of normal healthy cells. Therefore, delivering a drug in a concentrated way to a diseased cell specifically has the potential to reduce systemic side effects and side effects in other cells.

Hence, one obstacle to successful targeting of genes and proteins involved in disease, including cancer, is the development of a safe and effective method of delivering the therapeutic agent to the target.

SUMMARY OF THE INVENTION

It is an object of the invention to at least partly overcome the drawbacks of the existing technologies, and to provide a means of delivering a therapeutic agent, in particular an oligonucleotide, to target cells.

In a first aspect, these and other objects are achieved by a method of producing nanovesicles comprising an inhibitor oligonucleotide to an oncogene or a proto-oncogene or the gene product thereof, said method comprising a) introducing a DNA sequence encoding a nucleic acid capable of inhibiting a human oncogene or proto-oncogene or a gene product thereof, into a mammalian cell;

b) maintaining the cell under conditions allowing expression of said oligonucleotide inhibitor; and c) obtaining nanovesicles containing said oligonucleotide inhibitor from said cell.

The step of obtaining the nanovesicles may include isolation naturally released extracellular vesicles from the cell culture, and/or producing nanovesicles by extrusion of the cell through micro and/or nanofilters.

As used herein, "oncogene" refers to a gene that has the potential to cause cancer. In cancer cells, oncogenes are often mutated or expressed at high levels (upregulated or amplified). A "proto-oncogene" refers to a gene that can become an oncogene due to mutations or increased expression.

Examples of known proto-oncogenes include RAS, WNT, MYC, ERK, and TRK.

As used herein, "nanovesicle" refers to a cell-derived vesicle having a size in the nanometer range, and typically less than 500 nm. "Cell-derived vesicles" include extracellular vesicles or exosomes naturally released from cells, as well as vesicles produced from cells by serial extrusion of the cells through micro and/or nano filters, as described herein. Nanovesicles produced from cells by serial extrusion may be referred to as "artificial nanovesicles", however it should be noted that "artificial" in this context only means that the nanovesicles are not naturally released by the cells (as opposed to, for example, exosomes). Hence, "artificial" in this context does not suggest that the nanovesicles are synthetic; they are still cell-derived and are constituted of the same components as the cell from which the nanovesicle originated ("producer cell").

As used herein, "inhibit" means that the expression of a gene resulting in a functional gene product (e.g. a protein) is reduced, e.g. by inhibition of transcription, mRNA degradation, or inhibition of mRNA translation into protein. In the context of the present invention, the "inhibition" need not be complete; partial inhibition or repression or down-regulation may also provide a desirable effect.

As used herein, "oligonucleotide inhibitor" refers to an oligonucleotide which is an inhibitor, i.e. is capable of inhibiting a target molecule. It may also be referred to as an "oligonucleotide inhibitor".

The method present invention is advantageous, in particular compared to the use of synthetic delivery vehicles such as synthetic liposomes, since the production of nanovesicles can easily be scaled up by culturing more of the nanovesicle-producing cells, and the nanovesicles could be produced in large quantities at a suitable time-point, e.g. when the cell is expressing optimal levels of targeting molecule. Additionally, the nanovesicles obtained by the present invention, in particular the nanovesicles obtained by serial extrusion of the producer cells, may contain higher concentrations of the inhibitor oligonucleotide (higher loading capacity), and may be easier to load with an inhibitor oligonucleotide such as siRNA. Furthermore, various modification of the nanovesicles, e.g. by expression of targeting molecules on the surface, is enabled or at least greatly simplified. The method of the invention is also cost-effective, since a nanovesicle-producing cell culture can be scaled up by normal cell culturing, and also frozen, which reduces waste associated with shelf-life of the cells.

In embodiments of the invention the inhibitor oligonucleotide is an inhibitor to a human oncogenic or proto-oncogenic transcription factor. By targeting a transcription factor, many different malignancies could be repressed by one inhibitor. Preferably, the inhibitor oligonucleotide is may be an inhibitor to a human MYC gene or gene product, preferably the c-Myc gene or gene product, or an inhibitor to a member of the E2F gene family or a gene product thereof. In other embodiments, the inhibitor oligonucleotide may be an inhibitor to a human cellular signal transduction molecule lacking enzymatic activity, for example a member of the Ras family.

In embodiments of the invention, the oligonucleotide may be RNA, preferably an RNAi molecule. An RNAi molecule may be selected from the group consisting of shRNA, siRNA, miRNA, piRNA, nasiRNA or antisense RNA, or any other molecule with RNAi capacity.

In embodiments of the invention, the DNA sequence encoding an oligonucleotide capable of inhibiting a human oncogene or proto-oncogene may be a DNA sequence selected from the group consisting of SEQ ID NO: 1-92 and SEQ ID NO: 185-218, preferably selected from the group consisting of SEQ ID NO: 1-32, SEQ ID NO: 33-67, and SEQ ID NO: 185-218, more preferably selected from among SEQ ID NO: 1-10 and SEQ ID NO: 185-196.

In embodiments of the invention, the cell may express a targeting molecule on the cell surface.

As used herein, "targeting molecule" means a molecule capable of specifically binding to another molecule ("target molecule"). Hence, a targeting molecule may be used to specifically localize e.g. a cell or a vesicle presenting the targeting molecule on its surface to an entity, such as a cancer cell, presenting the target molecule.

The targeting molecule may be a ligand specifically binding to a surface protein that is overexpressed on cancer cells. Expression of targeting surface molecules in the nanovesicle-producing cells may provide tissue-specific targeting of the nanovesicles obtained from the cells. An advantage with making the producer cell express the targeting molecule is that the cell creates a membrane bound molecule that may be more efficient in interacting with targeting receptors, whereas the efficacy of liposome-engineered targeting often can fail.

Optionally, the method may comprise introducing a DNA sequence coding for a targeting molecule to be expressed on the cell surface, prior to step a) or simultaneously with step a).

In embodiments of the invention, the cell may express at least two different targeting molecules, which may further increase targeting specificity or otherwise improve the targeting of the cells and/or the nanovesicles to cancer cells.

Examples of suitable targeting molecules include epidermal growth factor (EGF), melanocyte-stimulating hormone (MSH) or a variable region of an antibody directed against a surface protein that is overexpressed on cancer cells, or a fab-fragment of said antibody.

In embodiments of the invention, the cell is a human cell and the oncogene or protooncogene is a human oncogene or proto-oncogene. In such embodiments, the human cell may be transfected or transduced with a genetic construct comprising a gene whose gene product functionally replaces the human oncogene or proto-oncogene naturally expressed by the human cell. For example, the human oncogene or proto-oncogene may be one member of the MYC gene family, and the genetic construct may comprise another member of the MYC gene family.

In embodiment of the invention, the cell may be transfected or transduced with a construct comprising the N-Myc or L-Myc genes and overexpresses N-Myc or L-Myc.

In embodiments of the invention, step a) of the above method may comprise introducing a genetic construct comprising said DNA sequence coding for an oligonucleotide capable of inhibiting human c-Myc, operatively linked to an inducible promoter, and step b) may comprise inducing expression by activation of said inducible promoter.

The method of producing nanovesicles according to the invention may be performed in in vitro or ex vivo.

In another aspect, the invention provides an isolated nanovesicle produced by the method described above.

As used herein, "isolated nanovesicle" refers to a nanovesicle that has at least been separated from the producer cell, typically separated from the producer cell culture or from a first filtrate obtained when producing artificial nanovesicles by serial extrusion through micro- or nanofilters as described below. Isolated nanovesicles are typically contained in a medium or composition, and may have been subject to one or more isolation or purification steps to remove e.g. cell debris or other components originating from cells, for example by centrifugation and/or filtration.

Although the present specification recites "a nanovesicle", it is understood that this term also encompasses a plurality of nanovesicles.

In a further aspect, the invention provides an isolated nanovesicle comprising an inhibitor oligonucleotide to a human oncogene or proto-oncogene, preferably a human oncogenic or proto-oncogenic transcription factor. In particular, the oncogene or proto-oncogene may be a member of the MYC gene family, and more preferably the gene encoding human c-Myc. Alternatively the oncogene or proto-oncogene may be a member of the E2F gene family, and more preferably a human gene encoding human E2f1, E2f2 or E2f3. As another example of, the oncogene or proto-oncogene may be a member of the RAS gene family, and more preferably a human gene encoding human H-Ras, N-Ras or K-Ras.

In embodiments of the invention the inhibitor oligonucleotide may be RNA, preferably an RNAi molecule. The RNAi molecule may be selected from the group consisting of shRNA, siRNA, miRNA, piRNA. nasiRNA or antisense RNA, or any other molecule with RNAi capacity. In some embodiments, the RNA may be shRNA or siRNA comprising a sequence selected from the group consisting of SEQ ID NO: 93-184, preferably selected from the group consisting of SEQ ID NO: 93-124 (targeting myc) and 125-159 (targeting E2f), for example selected from among SEQ ID NO: 93-102 (targeting c-myc).

However the oligonucleotide may also be DNA, e.g. an antisense oligonucleotide (ASO).

In a further aspect, the present invention provides a human cell transfected or transduced with a genetic construct comprising a gene whose gene product functionally replaces a human oncogene or proto-oncogene naturally expressed by said human cell. Hence, the producer cell may be modified to be independent on the normal, non-pathological expression of a gene intended to be inhibited by the inhibitor oligonucleotide. As a result, the growth and viability of the producer cell can be unaffected by the production of inhibitor oligonucleotide. In particular, the human oncogene or proto-oncogene may be one member of the MYC gene family, and the genetic construct introduced into the cells may be another member of the MYC gene family. For example, the human oncogene or proto-oncogene may be c-Myc and the genetic construct may comprise a gene coding for N-Myc or L-Myc.

In embodiments of the invention, the human cell may further comprise a DNA sequence coding for a inhibitor oligonucleotide to said oncogene or proto-oncogene.

In a further aspect, the invention provides a human cell transduced or transfected with a DNA sequence coding for an inhibitor oligonucleotide to a human oncogene or proto-oncogene, preferably a human oncogenic or proto-oncogenic transcription factor, wherein said DNA sequence is operably linked to an inducible promoter.

A human cell as comprising a DNA sequence coding for an inhibitor oligonucleotide to a human oncogene or proto-oncogene may be comprise a DNA sequence selected from the group consisting of SEQ ID NO: 1-92 and SEQ ID NO: 185-218, preferably selected from the group consisting of SEQ ID NO: 1-32, SEQ ID NO: 33-67, and SEQ ID NO: 185-218, more preferably selected from among SEQ ID NO: 1-9 and SEQ ID NO: 185-196.

In embodiments of the invention, the human cell may be a stem cell, preferably an embryonic stem cell or a mesenchymal stem cell.

In another aspect, the invention provides a non-human mammalian cell, transduced or transfected with a DNA sequence coding for an inhibitor oligonucleotide to a human oncogene or proto-oncogene.

The invention may be used for delivery of a therapeutic agent to a cell, in vitro or in vivo, e.g. for therapy. Hence, in another aspect the invention provides a method of delivering a inhibitor oligonucleotide against a human oncogene or proto-oncogene to a cell, comprising contacting said cell with a human cell or a nanovesicle as described above.

In embodiments, a method of delivering a inhibitor oligonucleotide against a human oncogene or proto-oncogene to a cancer cell in vivo, comprises the steps of a) administering to a patient having said cancer cell, a cell transduced or transfected with a DNA sequence coding for an inhibitor oligonucleotide to a human oncogene or proto-oncogene, wherein said DNA sequence is operably linked to an inducible promoter, and b) inducing expression of the inhibitor oligonucleotide by administration of a substance activating said inducible promoter.

Hence, nanovesicles as described herein may be used for treatment of cancer.

In yet another aspect, the invention relates to a composition comprising nanovesicles as described herein and a pharmaceutically acceptable carrier. The composition and/or the nanovesicles may be for use as a medicament, in particular for treatment of cancer. The cancer to be treated may be selected from the group consisting of malignant melanoma, colorectal cancer, ovarian cancer, breast cancer, renal cancer, gastrointestinal cancer, brain cancer, lung cancer, nasopharyngeal cancer, esophageal cancer, gastric cancer, liver cancer, cervical cancer, prostate cancer, non-Hodgkin lymphoma, Hodgkin lymphoma, nasal NK/T-cell lymphoma, sarcoma, leukemia, neuroendocrine cancers, midline carcinomas, neuroblastoma and cancers of the head and neck.

DETAILED DESCRIPTION OF THE INVENTION

The present invention is based on the realization that nanovesicles originating from cells, including mammalian cells, can be used as vehicles for the delivery of potentially therapeutic inhibitor molecules that target fundamental cellular functions, with increased efficacy and decreased risk for adverse side effects, compared to prior art delivery technologies.

In particular, the present inventors propose the use of cells and/or vesicles as described herein for delivery of nucleic acids that may selectively inhibit or repress the production of, or functionality of, an oncogene or proto-oncogene or a corresponding gene product, for example oncogenic or proto-oncogenic transcription factors and/or oncogenic or proto-oncogenic signaling molecules. The oncogene or proto-oncogene may be a non-mutated oncogene.

One family of oncogenes or proto-oncogenes of particular interest is the MYC gene family consisting of MYC, MYCN and MYCL. The MYC gene family encodes three different transcription factors, c-Myc (encoded by MYC), N-Myc (encoded by MYCN) and L-Myc (encoded by MYCL), respectively, which regulate a wide array of genes and cellular processes that are crucial in malignant disease. However, the MYC gene family is also active in normal cell proliferation.

The gene encoding c-Myc, MYC, is located on chromosome 8 in the human genome. The Myc protein acts though binding of Enhancer Box sequences (E-boxes) and also by recruiting histone acetyltransferases (HATs), thus regulating the chomatin structure. Myc is believed to regulate expression of 15% of all human genes.

c-Myc and N-Myc are downstream of mitogenic signals such as Wnt, Shh and EGF (via the MAPK/ERK pathway). Since these pathways are often activated by mutation of genes like APC (Wnt-pathway), PATCHED (Shh-pathway) and EGFR, BRAF, RAS, PTEN (EGF-pathway), c-Myc or N-Myc is induced in cancer cells.

MYC can also be activated by chromosomal translocation to a transcriptionally active chromosomal location, such as those of the Immunoglobulin locus in B lymphocytes and of the T-cell receptor in T lymphocytes. These translocation result in various hematological malignancies such as Burkitt lymphoma or T-acute lymphocytic leukemia.

An alternative activation of MYC family members is via amplification, which happens in various cancers including lung cancer (MYC, MYCN and MYCL), neuroblastoma (MYCN) and breast cancer (MYC).

By modifying expression of other genes, Myc activation results in numerous biological effects. The first to be discovered was its capability to stimulate metabolism; e.g. it stimulates the transcription of genes encoding ornithine decarboxylase and lactate dehydrogenase. Myc also drives cell proliferation (e.g. by upregulating cyclins, E2f transcription factors and downregulating p21), and it plays a very important role in regulating cell growth (upregulating ribosomal RNA and proteins), apoptosis (downregulating Bcl-2), differentiation and stem cell self-renewal.

Targeting the most common of the Myc proteins, c-Myc, with small molecules has been proven exceedingly difficult because the tertiary protein structure lacks pockets that could function as binding sites for small inhibitory molecules. However, it has been shown that the expression of Myc proteins can be blocked by RNAi molecules (Wang, H., et al., *c-Myc depletion inhibits proliferation of human tumor cells at various stages of the cell cycle*. Oncogene, 2008. 27(13): p. 1905-15).

One set of genes that are regulated downstream of Myc and other cell signaling pathways is the transcriptional activators of the E2F family. E2F1, E2F2 and E2F3A encode transcription factors that stimulate genes involved in cell cycle progression such as cyclin E and Cdk2, components of DNA replication (for example DNA polymerase, replication origin-binding protein HsOrc1, MCM 5 and cdc6) and nucleotide biogenesis (thymidine kinase and dihydrofolate reductase). The E2F family also contains transcriptional repressors (E2f3b and E2f4-8).

E2f activators are bound by the retinoblastoma protein pRB, encoded by the RB1 gene. When bound, E2f proteins are unable to stimulate cell cycle progression. To stimulate cell cycle progression, pRB is phosphorylated by cyclin-dependent kinases Cdk2, Cdk4 and Cdk6 on multiple sites. This releases bound E2f from pRB resulting in E2f activation. Cancer cells can exhibit elevated E2f activities because of many reasons including loss of the RB1 gene or the CDKN2A-C genes. The latter encode Cdk inhibitors p15, p16 and p18, collectively called Ink4 proteins, which inhibit Cdk4 and Cdk6. Other ways to activate constitutive E2f activity is by direct gene transcription of CDK4, CCND2 and even E2F1 genes by Myc proteins, or by Ink4-resistant mutations of Cdk4.

Targeting the most common of the E2f proteins, E2f1, with small molecules is difficult since it is a transcription factor and hence lack an enzymatic active site. However, it has been shown that the expression of E2f1 can be blocked by RNAi molecules in melanoma, resulting in cell cycle arrest and senescence. (Verhaegen et al. E2F1-Dependent Oncogenic Addiction of Melanoma Cells to MDM2 Oncogene. 2012 Feb. 16; 31(7)828-841)

In embodiments of the invention, signaling molecules targeted by the inhibitor molecule may be signaling molecules lacking enzymatic activity. The signaling molecules targeted by the inhibitor molecule may include signaling molecules involved in intracellular signal transduction, e.g. regulating cell growth, differentiation and survival, such as the Ras family of proteins, including Kras, Hras, and Nras.

According to embodiments the present invention, nanovesicles containing an inhibitor molecule can be produced in vitro, from animal cells grown in vitro, typically mammalian cells such as murine or human cells. The cells from which nanovesicles are produced are herein referred to as "producer cells". In embodiment of the invention, the nanovesicles may comprise exosomes and other extracellular vesicles naturally released from cells, as well as artificial vesicles produced by serial extrusions of cells through micro- and/or nano-filters. In other embodiments of the invention the nanovesicles are artificial nanovesicles, which may be produced by serial extrusions of cells through micro- and/or nano-filters. It is known that extruding cells through filters disintegrates the cells, and that the cell membrane and membrane fractions reassemble in the process. The yield of vesicles produced by such a method is much higher than that of naturally produced exosomes.

Artificial nanovesicles used in embodiments of the present invention may be produced by serial extrusions of producer cells, typically mammalian cells, through micro- and/or nano-filters. The nanovesicles may be produced by a method as described in US 2012/0177574, incorporated herein by reference, see in particular paragraphs [0173]-[0197]. The thus artificially produced nanovesicles retain the membrane structure of the producer cells, such as the lipid bilayer structure and membrane proteins including topology of the cell membrane surface molecules. Furthermore, the nanovesicles retain the same cytoplasmic components as the producer cell.

A nanovesicle according to embodiments of the invention may have a size up to 500 nm, for example up to 300 nm, such as up to 250 nm or 200 nm. For example, the nanovesicles may have a size in the range of 100-200 nm. However, in some embodiments the nanovesicles may be smaller than 100 nm, for example at least 50 nm or at least 80 nm.

In embodiments of the invention, exosomes and other vesicles, e.g. microvesicles, naturally produced and released by cells may also contain the inhibitor molecule and optionally also express a targeting molecule on its surface.

Exosomes, microvesicles and artificial nanovesicles have several similarities but there are also important differences between these vesicles. Exosomes are produced through a natural process, involving inward budding of the cell membrane and are formed via multivesicular bodies. Exosomes are loaded with very specific materials, including RNA, which is not a random selection of cellular content. Furthermore, exosomes are very tight structures, which have been shown to be difficult to load with external siRNAs (Wahlgren et al., Nucleic Acids Res. 2012 Sep. 1; 40(17):e130). Microvesicles, on the other hand, seem in some experiment to contain much less RNA than exosomes.

Artificial nanovesicles, produced by serial extrusions of cells through micro- and nanofilters, do contain any protein on their surface that the cell does not have, and also contains a random selection of the cytoplasm. Therefore, overexpression of targeting surface molecule in the cell membrane of an engineered cell will result in the presence of that molecule on the artificial nanovesicles. Similarly, a molecule overexpressed within the cell, will also be present within the artificial nanovesicle in high concentrations. Most importantly, the yield of artificial nanovesicles is expected to be significantly higher than the yield of exosomes or other extracellular vesicles naturally released by a cell.

In embodiments of the invention, the inhibitor molecule contained within the nanovesicles may be a nucleic acid, typically an RNAi molecule such as shRNA, siRNA or miRNA, and typically shRNA or siRNA.

RNA interference, referred to as RNAi, is a gene regulating mechanism occurring in many eukaryotic cells. RNAi is mediated by the Dicer enzyme, which cleaves a long double-stranded RNA molecule (dsRNA) into shorter stands of double stranded RNA, small interfering RNA (siRNA) The siRNA strands are separated into two single-stranded RNA molecules, ssRNAs, and the guide strand is incorporated into a complex called the RNA-induced silencing complex (RISC) and may silence gene expression by complementary binding to a mRNA molecule. The RNAi mechanism can be utilized for selective silencing of a gene of interest by genetically engineered expression in a cell of a small hairpin RNA molecule (shRNA), containing a nucleotide sequence designed to silence a particular mRNA, and which is subsequently cleaved by Dicer into siRNA.

As used herein, "RNAi molecule" typically refers to any RNA molecule involved in an RNAi process, including for example dsRNA, short hairpin RNA (shRNA, which may be used as a starting material instead of the dsRNA), miRNA, siRNA, and ssRNA.

The use of inhibitor oligonucleotides, and RNAi in particular, has many advantages over small molecule drugs. Small molecules exhibit problems with solubility, which render them impossible to formulate for in vivo delivery. Once formulated they may also exhibit problems with absorption, requiring delivery via intravenous, rather than an oral, route. The small molecule may also be bound by serum proteins or hindered from entering e.g. a tumor because of too high interstitial pressure, resulting in a poor distribution. Small molecules may also be distributed systemically, which results in a lower intra-tumoral concentration. Small molecules may also be metabolized, leading to decreased stability and the possible production of toxic bi-products. Decreased steady-state levels can also be the result of excretion. Finally, small molecules may have multiple targets and exhibit toxicity in a living multicellular organism. Oligonucleotides, on the other hand, are rapidly degraded into non-toxic residues.

In embodiments of the invention, the inhibitor molecule may be an RNAi molecule that can achieve inhibition of a member of the Myc family. In such embodiments, the inhibitor molecule may comprise an RNA sequence selected from among SEQ ID NO: 93-124, for example selected from SEQ ID NO: 93-102 (RNA targeting c-myc), SEQ ID NO: 103-111 (targeting L-myc), or SEQ ID NO: 112-124 (targeting N-myc).

In embodiments of the invention the inhibitor molecule may be an RNAi molecule that can achieve inhibition of a member of the E2F family, for example E2f1, E2f2 or E2f3. Such inhibitor molecules may comprise an RNA sequence selected from SEQ ID NO: 125-159, for example SEQ ID NO: 125-140 (targeting E2f1), SEQ ID NO: 141-148 (targeting E2f2), or SEQ ID NO: 149-159 (targeting E2f3).

In yet other embodiments of the invention the inhibitor molecule may be an RNAi molecule that can achieve inhibition of a member of the Ras family, for example Hras, Kras or Nras. Such inhibitor molecules may comprise an RNA sequence selected from SEQ ID NO: 160-184, for example selected from SEQ ID NO: 160-171 (targeting Hras), SEQ ID NO: 172-177 (targeting Kras) or SEQ ID NO: 178-184 (targeting Nras).

In order to produce nanovesicles having the desired content of inhibitor molecules, in particular RNAi molecules, such as shRNA or siRNA, a DNA sequence coding for the inhibitor molecule may be inserted into the producer cell using conventional genetic engineering techniques, e.g. using a viral vector. Vectors suitable for obtaining e.g. shRNA expression in animal, e.g. mammalian, cells are known to a person skilled in the art, and may include vectors based on adeno-associated viruses, adenoviruses or retroviruses/lentiviruses.

Hence, a DNA sequence encoding the inhibitor molecule of interest may be introduced into the producer cells, which may be maintained under conditions allowing the expression of the DNA sequence, i.e. production of the inhibitor molecule within the producer cells. By introduction of a DNA sequence encoding the inhibitor molecule, the inhibitor molecule may be expressed at high quantities within the producer cell and localized to the cytosol. For example, shRNA encoded by a DNA sequence is translocated by the cellular machinery to the cytosol, where it may be processed into siRNA. When the inhibitor molecule is expressed and present within cytosolic compartment of the producer cell, the inhibitor molecule will also be present in nanovesicles produced from the cells, since the nanovesicles have the same cytosolic composition as the producer cell. The nanovesicles produced from cells expressing a shRNA will thus contain, for example, shRNA and/or siRNA originating from the shRNA, typically siRNA.

Alternatively, an inhibitor molecule, such as an oligonucleotide, can be loaded directly into isolated nanovesicles.

In embodiments of the invention, the inhibitor molecule is an RNAi molecule, typically shRNA or siRNA, for inhibition or repression of a human MYC gene or gene product.

To express an RNAi molecule such as shRNA against human c-Myc, a DNA sequence may be introduced in the producer cell comprising a sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID. NO: 8, and SEQ ID NO: 9; alternatively, a DNA sequence may be introduced which is selected from the group consisting of SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, and SEQ ID NO: 196.

To express an RNAi molecule such as shRNA against human L-Myc, a DNA sequence may be introduced in the producer cell comprising a sequence selected from SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 19. Alternatively, a DNA sequence may be introduced which is selected from the group consisting of SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, and SEQ ID NO: 205.

To express an RNAi molecule such as shRNA or siRNA against human N-Myc, a DNA sequence may be introduced in the producer cell comprising a sequence selected from SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, and SEQ ID NO: 32. Alternatively, a DNA sequence may be introduced which is selected from the group consisting of SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, and SEQ ID NO: 218.

Lentiviral plasmids containing the DNA sequences of SEQ ID NO: 185-218 are commercially available from Sigma Aldrich (USA).

In embodiments of the invention, the inhibitor molecule is an RNAi molecule, typically shRNA or siRNA, for inhibition or repression of a human E2F gene or gene product. To express an RNAi molecule such as shRNA against human E2f1, a DNA sequence may be introduced in the producer cell comprising a sequence selected from SEQ ID NO: 33-48. To express an RNAi molecule such as shRNA against human E2f2, a DNA sequence may be introduced in the producer cell comprising a sequence selected from SEQ ID NO: 49-56. To express an RNAi molecule such as shRNA against human E2f3, a DNA sequence may be introduced in the producer cell comprising a sequence selected from SEQ ID NO: 57-67.

In embodiments of the invention, the inhibitor molecule is an RNAi molecule, typically shRNA or siRNA, for inhibition or repression of a human RAS gene or gene product. To express an RNAi molecule such as shRNA against human Hras, a DNA sequence may be introduced in the producer cell comprising a sequence selected from SEQ ID NO: 68-79. To express an RNAi molecule such as shRNA against human Kras, a DNA sequence may be introduced in the producer cell comprising a sequence selected from SEQ ID NO: 80-85. To express an RNAi molecule such as shRNA against human Nras, a DNA sequence may be introduced in the producer cell comprising a sequence selected from SEQ ID NO: 86-92.

The DNA sequence coding for the inhibitor molecule is typically under the control of a promoter. The promoter may be a constitutive promoter or an inducible promoter.

In embodiments of the invention, for example where the producer cells are human cells dependent of a functional human c-Myc protein for their own proliferation, it may be preferable to use an inducible promoter, so that expression of the inhibitor molecule can be initiated at a suitable point in time, such as when a desired number of producer cells or a desirable producer cell density has been achieved. Any suitable conventional promoter may be used, for example a doxycyclin-inducible promoter.

In other embodiments, the producer cells may be independent of the function of the target gene which the inhibitor molecule is intended to inhibit or repress. In such embodiments, the promoter may be a constitutive promoter or an inducible promoter. As used herein "target gene" refers to a gene to be inhibited or repressed by the inhibitor molecule, or while gene product is to be inhibited or repressed by the inhibitor molecule.

For example, non-human animal cells or bacteria may be used as producer cells for the production of nanovesicles containing an inhibitor molecule directed to a human gene or gene product. For instance, mouse cells may be used for production of an RNAi molecule (and nanovesicles containing the RNAi molecule) against a human gene, e.g. a member of the human MYC gene family, such as human c-Myc, at least where the murine and human genes do not have too high sequence similarity. Alternatively, producer cells of the same species as the target gene may be used, which has been modified to be independent on the target gene. As an example, human cells to be used for the production of an RNAi molecule against a first member of the MYC family may be modified to overexpress another member of the MYC gene family, so that it is made independent on the functionality of the first MYC member. In particular, human cells may be genetically modified using standard techniques to overexpress N-myc, which is normally expressed only at low levels, which may functionally replace c-Myc and render the cells independent of c-Myc. Hence, expression of an RNAi molecule against human c-MYC within the same producer cells will not disrupt cell growth and proliferation. Alternatively, the native c-Myc of a human cell may be genetically modified, e.g. by introduction of one or more point mutations so as to avoid complementarity with an RNAi molecule directed against human c-Myc and thus avoid inhibition of the c-Myc of the producer cell.

In embodiments of the invention, nanovesicles may be produced from cells as described above, without insertion of a DNA sequence encoding the inhibitor molecule. In such embodiments, the inhibitor molecule may be introduced ("loaded") directly into the isolated nanovesicles using electroporation or the like. For example, an RNAi molecule such as siRNA may be inserted directly into isolated nanovesicles by electroporation. Previous studies suggest that that this approach may be efficient for delivery into exosomes (Alvarez-Erviti, L., et al., *Delivery of siRNA to the mouse brain by systemic injection of targeted exosomes*. Nat Biotechnol, 2011. 29(4): p. 341-5;).

The cells used as producer cells in the present invention may be any eukaryotic cell that is capable of forming nanovesicles and which is susceptible of expressing an inhibitor molecule. Typically, the cells may be animal cell, in particular mammalian cells, including murine and human cells. Further, the cells used as producer cells may originate from a cell line suitable for in vitro proliferation, modification and expression of the inhibitor molecule, and production of the nanovesicles. The cells may be stem cells. Examples of suitable cells include human embryonic kidney (HEK, e.g. HEK 293) cells, mesenchymal stem cells, fibroblasts (e.g. NIH 3T3 mouse fibroblasts), or any other suitable eukaryotic cells. Mesenchymal stem cells may be produced either from other cells, such as embryonic cells, or by autologous means (thus from the patient for which the therapy is intended)

In order to achieve selective delivery of the nanovesicles to a cancer cell, the nanovesicles may have a targeting molecule present on the outer surface of its membrane. Preferably, the targeting molecule may be a molecule, e.g. a ligand, which selectively binds to another molecule, e.g. a ligand receptor, that is specific to the surface of cancer cells or overrepresented (overexpressed) on the surface of cancer cells. Examples of suitable targeting molecules include epidermal growth factor (EGF), which binds to the EGF receptor (EGFR), and melanocyte-stimulating hormone (MSH), which binds to the MSH receptor (MSHR; also called melanocortin 1 receptor, MC1R). EGFR is overexpressed on a majority of epithelial cancer cell types, whereas MC1R is expressed on melanoma and cells of the melanocyte lineage. Recently, it was shown that exosomes that overexpress EGF-like peptides, using the transmembrane domain of platelet-derived growth factor, can target to EGFR expressing tumors in vivo in mouse (Ohno, S. I., et al., *Systemically Injected Exosomes Targeted to EGFR Deliver Antitumor MicroRNA to Breast Cancer Cells*. Mol Ther, 2012). Targeting molecules can also include natural ligands or even engineered antibody fragments possessing the ability to bind cancer-specific surface antigens.

To introduce the targeting molecule into the nanovesicles, a DNA sequence comprising a DNA sequence, such as a gene, encoding the targeting molecule may be introduced using conventional cloning techniques, including any sequences such as a promoter etc. necessary to achieve expression of the targeting molecule within the cell. The targeting molecule may be a molecule that locates naturally to the outer surface of the cell membrane. Alternatively, the targeting molecule may be a fusion protein with a transmembrane protein, such as a GPI-anchored protein or the transmembrane/cytosolic domain of ICAM-1 (T/C ICAM-1).

When the targeting molecule is localized to the cell membrane, the targeting molecule will also form part of the nanovesicle membrane after isolation of nanovesicles as described above. Genetic modification of a producer cell to express a targeting molecule on the surface of the cell membrane may be carried out before the step of introducing a DNA sequence encoding the inhibitor molecule into the producer cell. Alternatively, in embodiments of the invention, the DNA sequence encoding the targeting molecule and the DNA sequence encoding the inhibitor molecule may be introduced into the producer cell simultaneously. Introduction of a targeting molecule on the surface of the producer cell and hence also on its naturally occurring extracellular vesicles, or the nanovesicles produced by serial extrusion through membranes, may be performed also in embodiments where the producer cells do not express the inhibitor molecules, and the nanovesicles are isolated and subsequently used for direct introduction of an inhibitor molecule e.g. via electroporation.

The present invention offers a means to develop successful therapies against numerous diseases, including cancers. Nanovesicles according to embodiments of the invention may be administered to a patient suffering from a cancer caused at least partly by the oncogene or proto-oncogene against which the inhibitor molecule is directed. The nanovesicles may be administered via intravenous injection or directly into tumors, or into tumor-containing organs or parts of the body afflicted by tumors, optionally as part of a pharmaceutical composition.

A pharmaceutical composition may comprise the nanovesicles and typically also a pharmaceutically acceptable carrier. Examples of pharmaceutical compositions suitable for injection include sterile aqueous solutions or dispersions and sterile powders for the extemporaneous preparation of sterile injectable solutions or dispersions. Typically the composition is sterile. Further, the composition may be fluid to the extent that easy syringeability exists. Preferably, the composition is stable under the conditions of manufacture and storage, and it is preferably preserved against the contaminating action of microorganisms, such as bacteria and fungi.

Administration of a pharmaceutical composition according to embodiments of the invention may be effected via any suitable route, for example intravenous, intradermal, intramuscular, into brain, into spinal fluid, subcutaneous, directly into tumors or tumor infested tissues, or limbs, or intraocular, or intranasal, or by inhalation, or oral and/or intraperitoneal.

The nanovesicles may be internalized by cancer cells in a way similar to exosomes and other vesicles, and hence deliver their cargo of inhibitor molecule to the interior of a cancer cell, where the inhibitor molecule can perform its inhibitor function, e.g. via RNAi.

Additionally or alternatively, producer cells according to embodiments of the invention may be administered directly to a patient, for example directly into a tumor, without prior isolation of nanovesicles. In such cases, the cells preferably express a targeting molecule on the cell surface, so that they are localized in close vicinity to cancer cells after administration. Administration may be effected via any suitable route, for example intravenous, intradermal, intramuscular, into brain, into spinal fluid, subcutaneous, directly into tumors or tumor infested tissues, or limbs, or intraocular, or intranasal, or by inhalation, or oral and/or intraperitoneal. Further, in such cases the DNA sequence encoding the molecule inhibitor is preferably under the control of an inducible promoter, such as a promoter inducible by doxycyclin. After administration of the cells, expression of the inhibitor molecule may be induced by administration of doxycyclin to the patient by any suitable route, e.g. orally or intravenously. Upon expression of an RNAi molecule, the cells will be stressed and as a result release high amounts of exosomes and other vesicles during a short period of time, which will lead to high concentration of RNAi containing vesicles in the vicinity of the tumor cells, which then through natural means will take up the vesicles, and the RNAi molecule will have its therapeutic effect inside of the tumor cell by inhibiting crucial proto-oncogenes such as c-Myc or other transcription factors. High and/or prolonged expression of the inhibitor molecule in the injected cell will most likely induce apoptosis, which can result in further release of the molecule inhibitor from the cell via apoptotic bodies, which also can deliver their cargo to recipient tumor cells. As a result, the RNAi molecule will be encapsulated in naturally occurring nano- and microvesicles in the close vicinity of tumor cells, and will subsequently enter the cancer cells and elicit RNAi. The encapsulation of the RNAi molecule into vesicles is important, since the RNAi molecules would be naturally degraded if present as free molecules in the interstitial tissue (extracellularly).

The present invention offers a therapeutic tool that could potentially be used in the treatment of numerous cancerous diseases. The c-Myc gene may be overexpressed in as much as 80% of all cancers (Nilsson & Cleveland Oncogene. 2003 Dec. 8; 22(56):9007-21).

One example of a cancer that could be treated using cells or nanovesicles according to embodiments of the present invention is melanoma. It has previously been shown that c-Myc inhibition can be efficient in causing senescence in a majority of malignant human melanoma cell lines (Wang et al., 2008). Further, Myc inhibition by systemic expression of a dominant-interfering Myc mutant in a mouse model of Ras-induced lung adenocarcinoma, triggers rapid regression of incipient and established lung tumors, confirming that targeting Myc may be efficient in treatment of malignancy (Soucek, L., et al., Modelling Myc inhibition as a cancer therapy. Nature, 2008. 455(7213): p. 679-83). Together, these previous studies suggest that many malignancies including melanoma are dependent on c-Myc.

A nanovesicle according to embodiments of the invention that a) targets malignant melanoma cells, and b) contains an RNAi molecule that down-regulates a downstream oncogene or a crucial transcription factor for the melanoma cells, may therefore be possible to utilize in metastatic uveal melanoma, as well as metastatic skin melanomas, regardless of oncogene mutation status. The c-Myc and E2f1 genes are believed to be very suitable target genes for such therapy, as they has been proven to be crucial in melanoma in general. Lastly, a melanoma-targeting cell or nanovesicle could possibly also be used as local therapy in the eye in uveal melanoma without metastasis, or as adjuvant therapy together with local removal of tumor, possibly avoiding enucleation.

c-Myc has also been associated with carcinoma of the cervix, colon, breast, lung and stomach, and the invention may thus also be useful in therapy of such malignancies.

Hence, in addition to melanoma, cells and/or nanovesicles targeting for example EGFR positive malignancies and containing an inhibitor to c-Myc, can be a putative therapeutic approach for many malignant diseases.

EXAMPLES

Example 1

Introducing Targeting Molecule on the Surface of Human Producer Cells

Firstly, pCMV-zeo vectors expressing EGF or MSH in frame with either a GPI-anchor protein or I-CAM1 are created and transfected into HEK 293 cells or mesenchymal stem cells. The transfected cells are treated with zeocin and resistant cells are sorted based on surface expression of EGF or MSH using magnetic beads or a cell sorter. Maintenance of the transgenic expression may be routinely monitored with flow cytometry.

The cells expressing EGF or MSH fusion proteins may be further used for production of nanovesicles, optionally with expression of an inhibitor molecule.

Example 2

Production of Nanovesicles Using Human Cells Modified to be Independent of c-Myc A. Modification of Human Cells to Become Independent on c-Myc A mammalian expression vector containing a murine retrovirus receptor (mCAT-1) and an N-Myc:GFP fusion separated by an IRES (to enable cap-independent translation) is transfected into HEK 293T cells or mesenchymal stem cells. The cell line used may be equipped with an ecotropic receptor for murine-specific envelope-pseudotyped lentivirus to increase personnel safety. Further, by using a pcDNA-neo vector for the cloning it is possible to also express a neomycin resistance cassette. Alternatively, instead of an N-Myc gene the expression vector may contain an L-myc gene, if the inhibitor is directed to c-Myc.

The vector is cloned into human cells using the Amaxa nucleofector, or any other suitable methodology. Successfully transduced cells are selected with neomycin and FACS sort for GFP positive cells.

B. Introduction of a DNA Sequence Encoding an Inhibitor to a Human Myc Protein into the Nanovesicle-Producing Cells A lentiviral plasmid obtained from Sigma Aldrich, USA (MISSION TRCpLKO-puro clones) having a sequence selected from the group consisting of SEQ ID NO: 185-196 is transfected into HEK 293T cells. When transfected into cells HIV-1 based transcripts are generated which have been made replication-incompetent and self-inactivating by a deletion in the 3'-long terminal repeat. Further, the lentiviral vector is co-transfected with pCMV-dR8.2 dvpr and pHCMV-Eco (both from the Addgene plasmid depository), the former containing a minimal vector expressing HIV-GAG and the latter an eco-tropic envelope. The HEK 293T cells will thus produce lentivirus that are replication-incompetent and can only infect murine cells or cells expressing the murine retrovirus receptor (mCAT1) as in Example 2A. Next, the HEK 293T cells are cultured and virus-containing cell culture supernatant from the transfected cells is used to transduce mCAT1-expressing human cells, followed by selection with puromycin (encoded by lentivirus plasmid).

Since the mCAT1-expressing human cells depend on the N-Myc gene and not on the human target gene, e.g. c-Myc, their growth or viability may be unaffected by the expression of an inhibitor molecule directed against a human target gene, e.g. human c-Myc.

C. Isolation of Nanovesicles

Isolation of nanovesicles, and or naturally occurring extracellular vesicles, can be performed by known procedures, which includes centrifugation steps. For example, artificial nanovesicles may be produced as described in US 2012/0177574. Artificial high-density vesicles, emerging from nuclear membranes can be removed by a brief centrifugation steps. Nanovesicles expressing the molecule that targets for example the EGF receptor may be purified either by positive or negative selection, using either advanced FACS sorting protocols, magnetic methods or any other method, using antibody technology.

Example 3

Production of Nanovesicles Using Human Cells (Inducible Expression)

A. Introduction of a DNA Sequence Encoding an Inhibitor Against a Myc Protein (Inducible Expression) into Human Cells A tetracycline (doxycycline) or IPTG-inducible expression system is used for cloning the DNA sequence of the desired inhibitor molecule (here a DNA sequence according to any one of SEQ ID NO: 185-218. For example, the pLKO-TetON-puro system (Addgene) or the pLKO_IPTG_3×LacO system (Sigma) may be used.

B. Isolation of Nanovesicles (Optional)

Isolation of nanovesicles, and or naturally occurring extracellular vesicles, can be performed by known procedures, which includes centrifugation steps. For example, artificial nanovesicles may be produced as described in US 2012/0177574. Artificial high-density vesicles, emerging from nuclear membranes can be removed by a brief centrifugation steps. Nanovesicles expressing the molecule that targets for example the EGF receptor may be purified either by positive or negative selection, using either advanced FACS sorting protocols, magnetic methods or any other method, using antibody technology.

Alternatively, instead of isolating nanovesicles, the inhibitor molecule may be recovered from the cell culture and used later for direct introduction into nanovesicles e.g. using electroporation. In such embodiments, the inhibitor molecules may be introduced into artificially produced nanovesicles as described above.

Alternatively, in stead of using producing artificial nanovesicles by sequential extrusion, extracellular vesicles that are naturally released from the engineered producer cell, for example exosomes, microvesicles or apoptotic bodies, may be isolated from the cell culture. Such natural extracellular vesicles will express both the targeting molecule on its surface, as well as contain the inhibitor molecule.

Example 4

Production of Nanovesicles Using Murine Cells

A. Introduction of DNA Sequence Encoding a Myc Inhibitor into Murine Cells

A lentiviral plasmid obtained from Sigma Aldrich, USA (MISSION TRCpLKO-puro clones) having a sequence selected from the group consisting of SEQ ID NO: 185-218 is transfected into HEK 293T cells. When transfected into cells HIV-1 based transcripts are generated which have been made replication-incompetent by a deletion in the 3'-long terminal repeat. Further, the lentiviral vector is co-transfected with pCMV-dR8.2 dvpr and pHCMV-Eco (both from the Addgene plasmid depository), the former containing a minimal vector expressing HIV-GAG and the latter an eco-tropic envelope. The HEK 293T cells will thus produce lentivirus that are replication-incompetent and can only infect murine cells. Next, the HEK 293T cells are cultured and virus-containing cell culture supernatant from the transfected cells is used to transduce NIH 3T3 mouse fibroblasts, followed by selection with puromycin (encoded by lentivirus plasmid). Since the mouse fibroblasts depend on their native mouse gene and not on the human target gene, e.g. c-Myc, their growth or viability may be unaffected by the expression of an inhibitor molecule directed against a human target gene, e.g. human c-Myc.

B. Isolation of Nanovesicles

Isolation of nanovesicles, and/or naturally occurring extracellular vesicles, can be performed by known procedures, which includes centrifugation steps. For example, artificial nanovesicles may be produced as described in US 2012/0177574. Artificial High-density vesicles, emerging from nuclear membranes can be removed by a brief centrifugation steps. Nanovesicles expressing the molecule that targets for example the EGF receptor may be purified either by positive or negative selection, using either advanced FACS sorting protocols, magnetic methods or any other method, using antibody technology.

The invention claimed is:

1. A method of producing nanovesicles comprising an inhibitor oligonucleotide to an oncogene or a proto-oncogene or the gene product thereof, said method comprising
   (a) transfecting or transducing a mammalian cell with a construct comprising L-Myc genes;
   (b) maintaining the cell under conditions allowing the cell to overexpress L-Myc;
   c) introducing into the cell a DNA sequence encoding an oligonucleotide capable of inhibiting a human oncogenic or proto-oncogeneic transcription factor wherein said inhibitor does not inhibit L-Myc; and
   (d) obtaining nanovesicles containing said inhibitor oligonucleotide from said cell.

2. A method according to claim 1, wherein said inhibitor oligonucleotide is an inhibitor to a human MYC gene or gene product, preferably the c-Myc gene or gene product.

3. A method according to claim 1, wherein said oligonucleotide is RNA, preferably an RNAi molecule.

4. A method according to claim 3, wherein said DNA sequence encoding an oligonucleotide capable of inhibiting a human oncogenic or proto-oncogenic transcription factor is a DNA sequence selected from the group consisting of SEQ ID NO: 1-9.

5. A method according to claim 1, wherein said cell expresses a targeting molecule on the cell surface.

6. A method according to claim 1, wherein the method comprises, prior to step (c) or simultaneously with step (c), introducing a DNA sequence encoding a targeting molecule to be expressed on the cell surface.

7. A method according to claim 5, wherein said targeting molecule is a ligand specifically binding to a surface protein that is overexpressed on cancer cells.

8. A method according to claim 7, wherein said targeting molecule is epidermal growth factor (EGF), melanocyte-stimulating hormone (MSH) or a variable region of an antibody directed against a surface protein that is overexpressed on cancer cells, or a fab-fragment of said antibody.

9. A method according to claim 1, wherein the cell is a human cell.

10. A method according to claim 1, wherein step (c) comprises introducing a genetic construct comprising said DNA sequence coding for an oligonucleotide capable of inhibiting human c-Myc, operatively linked to an inducible promoter, and inducing expression by activation of said inducible promoter.

11. A method according to claim 1, performed in vitro or ex vivo.

12. A method according to claim 3, wherein said DNA sequence encoding an oligonucleotide capable of inhibiting a human oncogenic or proto-oncogenic transcription factor is a DNA sequence selected from the group consisting of SEQ ID NO: 185-196.

* * * * *

SEQUENCE LISTING

```
<160> NUMBER OF SEQ ID NOS: 218

<210> SEQ ID NO 1
<211> LENGTH: 21
<212> TYPE: DNA
<213> ORGANISM: Artificial Sequence
<220> FEATURE:
<223> OTHER INFORMATION: c-Myc DNA target sequence

<400> SEQUENCE: 1
cagttgaaac acaaacttga a                                              21

<210> SEQ ID NO 2
<211> LENGTH: 21
<212> TYPE: DNA
<213> ORGANISM: Artificial Sequence
<220> FEATURE:
<223> OTHER INFORMATION: c-Myc DNA target sequence

<400> SEQUENCE: 2
ccataatgta aactgcctca a                                              21

<210> SEQ ID NO 3
<211> LENGTH: 21
<212> TYPE: DNA
<213> ORGANISM: Artificial Sequence
<220> FEATURE:
<223> OTHER INFORMATION: c-Myc DNA target sequence

<400> SEQUENCE: 3
caggaactat gacctcgact a                                              21

<210> SEQ ID NO 4
<211> LENGTH: 21
<212> TYPE: DNA
<213> ORGANISM: Artificial Sequence
<220> FEATURE:
<223> OTHER INFORMATION: c-Myc DNA target sequence

<400> SEQUENCE: 4
gcttcaccaa caggaactat g                                              21

<210> SEQ ID NO 5
<211> LENGTH: 21
<212> TYPE: DNA
<213> ORGANISM: Artificial Sequence
<220> FEATURE:
<223> OTHER INFORMATION: c-Myc DNA target sequence

<400> SEQUENCE: 5
```

-continued

```
actgaaagat ttagccataa t                                              21

<210> SEQ ID NO 6
<211> LENGTH: 21
<212> TYPE: DNA
<213> ORGANISM: Artificial Sequence
<220> FEATURE:
<223> OTHER INFORMATION: c-Myc DNA target sequence

<400> SEQUENCE: 6
ccagaggagg aacgagctaa a                                              21

<210> SEQ ID NO 7
<211> LENGTH: 21
<212> TYPE: DNA
<213> ORGANISM: Artificial Sequence
<220> FEATURE:
<223> OTHER INFORMATION: c-Myc DNA target sequence

<400> SEQUENCE: 7
tacggaactc ttgtgcgtaa g                                              21

<210> SEQ ID NO 8
<211> LENGTH: 21
<212> TYPE: DNA
<213> ORGANISM: Artificial Sequence
<220> FEATURE:
<223> OTHER INFORMATION: c-Myc DNA target sequence

<400> SEQUENCE: 8
cctgagacag atcagcaaca a                                              21

<210> SEQ ID NO 9
<211> LENGTH: 21
<212> TYPE: DNA
<213> ORGANISM: Artificial Sequence
<220> FEATURE:
<223> OTHER INFORMATION: c-Myc DNA target sequence

<400> SEQUENCE: 9
atcatcatcc aggactgtat g                                              21

<210> SEQ ID NO 10
<211> LENGTH: 21
<212> TYPE: DNA
<213> ORGANISM: Artificial Sequence
<220> FEATURE:
<223> OTHER INFORMATION: c-Myc DNA target sequence

<400> SEQUENCE: 10
actcggtgca gccgtatttc t                                              21

<210> SEQ ID NO 11
<211> LENGTH: 21
<212> TYPE: DNA
<213> ORGANISM: Artificial Sequence
<220> FEATURE:
<223> OTHER INFORMATION: L-Myc DNA target sequence

<400> SEQUENCE: 11
cctgtgccac taaactacat t                                              21

<210> SEQ ID NO 12
<211> LENGTH: 21
<212> TYPE: DNA
```

-continued

```
<213> ORGANISM: Artificial Sequence
<220> FEATURE:
<223> OTHER INFORMATION: L-Myc DNA target sequence

<400> SEQUENCE: 12
cgaggacatc tggaagaaat t                                              21

<210> SEQ ID NO 13
<211> LENGTH: 21
<212> TYPE: DNA
<213> ORGANISM: Artificial Sequence
<220> FEATURE:
<223> OTHER INFORMATION: L-Myc DNA target sequence

<400> SEQUENCE: 13
cattggctct tctcaagctc t                                              21

<210> SEQ ID NO 14
<211> LENGTH: 21
<212> TYPE: DNA
<213> ORGANISM: Artificial Sequence
<220> FEATURE:
<223> OTHER INFORMATION: L-Myc DNA target sequence

<400> SEQUENCE: 14
caggaactac gcctccatca t                                              21

<210> SEQ ID NO 15
<211> LENGTH: 21
<212> TYPE: DNA
<213> ORGANISM: Artificial Sequence
<220> FEATURE:
<223> OTHER INFORMATION: L-Myc DNA target sequence

<400> SEQUENCE: 15
cccaagcgac tcgggtaagg a                                              21

<210> SEQ ID NO 16
<211> LENGTH: 21
<212> TYPE: DNA
<213> ORGANISM: Artificial Sequence
<220> FEATURE:
<223> OTHER INFORMATION: L-Myc DNA target sequence

<400> SEQUENCE: 16
tggcgcttag agaggacaat a                                              21

<210> SEQ ID NO 17
<211> LENGTH: 21
<212> TYPE: DNA
<213> ORGANISM: Artificial Sequence
<220> FEATURE:
<223> OTHER INFORMATION: L-Myc DNA target sequence

<400> SEQUENCE: 17
tgttggtaaa cagtttggaa a                                              21

<210> SEQ ID NO 18
<211> LENGTH: 21
<212> TYPE: DNA
<213> ORGANISM: Artificial Sequence
<220> FEATURE:
<223> OTHER INFORMATION: L-Myc DNA target sequence

<400> SEQUENCE: 18
tctccagttg gctttacttt a                                              21
```

<210> SEQ ID NO 19
<211> LENGTH: 21
<212> TYPE: DNA
<213> ORGANISM: Artificial Sequence
<220> FEATURE:
<223> OTHER INFORMATION: L-Myc DNA target sequence

<400> SEQUENCE: 19
gaggcttaga gatagacaat c                                             21

<210> SEQ ID NO 20
<211> LENGTH: 21
<212> TYPE: DNA
<213> ORGANISM: Artificial Sequence
<220> FEATURE:
<223> OTHER INFORMATION: N-Myc DNA target sequence

<400> SEQUENCE: 20
cagcagcagt tgctaaagaa a                                             21

<210> SEQ ID NO 21
<211> LENGTH: 21
<212> TYPE: DNA
<213> ORGANISM: Artificial Sequence
<220> FEATURE:
<223> OTHER INFORMATION: N-Myc DNA target sequence

<400> SEQUENCE: 21
gcgtcgcaga aaccacaaca t                                             21

<210> SEQ ID NO 22
<211> LENGTH: 21
<212> TYPE: DNA
<213> ORGANISM: Artificial Sequence
<220> FEATURE:
<223> OTHER INFORMATION: N-Myc DNA target sequence

<400> SEQUENCE: 22
ctgagcgatt cagatgatga a                                             21

<210> SEQ ID NO 23
<211> LENGTH: 21
<212> TYPE: DNA
<213> ORGANISM: Artificial Sequence
<220> FEATURE:
<223> OTHER INFORMATION: N-Myc DNA target sequence

<400> SEQUENCE: 23
gccagtatta gactggaagt t                                             21

<210> SEQ ID NO 24
<211> LENGTH: 21
<212> TYPE: DNA
<213> ORGANISM: Artificial Sequence
<220> FEATURE:
<223> OTHER INFORMATION: N-Myc DNA target sequence

<400> SEQUENCE: 24
cggacgaaga tgacttctac t                                             21

<210> SEQ ID NO 25
<211> LENGTH: 21
<212> TYPE: DNA
<213> ORGANISM: Artificial Sequence
<220> FEATURE:

<223> OTHER INFORMATION: N-Myc DNA target sequence

<400> SEQUENCE: 25
cacctccatg acagcgctaa a                                              21

<210> SEQ ID NO 26
<211> LENGTH: 21
<212> TYPE: DNA
<213> ORGANISM: Artificial Sequence
<220> FEATURE:
<223> OTHER INFORMATION: N-Myc DNA target sequence

<400> SEQUENCE: 26
cttctacccg gacgaagatg a                                              21

<210> SEQ ID NO 27
<211> LENGTH: 21
<212> TYPE: DNA
<213> ORGANISM: Artificial Sequence
<220> FEATURE:
<223> OTHER INFORMATION: N-Myc DNA target sequence

<400> SEQUENCE: 27
agacagcagc agttgctaaa g                                              21

<210> SEQ ID NO 28
<211> LENGTH: 21
<212> TYPE: DNA
<213> ORGANISM: Artificial Sequence
<220> FEATURE:
<223> OTHER INFORMATION: N-Myc DNA target sequence

<400> SEQUENCE: 28
catacctaag tactgtaata a                                              21

<210> SEQ ID NO 29
<211> LENGTH: 21
<212> TYPE: DNA
<213> ORGANISM: Artificial Sequence
<220> FEATURE:
<223> OTHER INFORMATION: N-Myc DNA target sequence

<400> SEQUENCE: 29
tcggacttgc tagacgcttc t                                              21

<210> SEQ ID NO 30
<211> LENGTH: 21
<212> TYPE: DNA
<213> ORGANISM: Artificial Sequence
<220> FEATURE:
<223> OTHER INFORMATION: N-Myc DNA target sequence

<400> SEQUENCE: 30
acgtccgctc aagagtgtca t                                              21

<210> SEQ ID NO 31
<211> LENGTH: 21
<212> TYPE: DNA
<213> ORGANISM: Artificial Sequence
<220> FEATURE:
<223> OTHER INFORMATION: N-Myc DNA target sequence

<400> SEQUENCE: 31
cacggagatg ctgcttgaga a                                              21

```
<210> SEQ ID NO 32
<211> LENGTH: 21
<212> TYPE: DNA
<213> ORGANISM: Artificial Sequence
<220> FEATURE:
<223> OTHER INFORMATION: N-Myc DNA target sequence

<400> SEQUENCE: 32
acgtgccgga gttggtaaag a                                              21

<210> SEQ ID NO 33
<211> LENGTH: 21
<212> TYPE: DNA
<213> ORGANISM: Artificial Sequence
<220> FEATURE:
<223> OTHER INFORMATION: E2f1 DNA target sequence

<400> SEQUENCE: 33
taactgcact ttcggccctt t                                              21

<210> SEQ ID NO 34
<211> LENGTH: 21
<212> TYPE: DNA
<213> ORGANISM: Artificial Sequence
<220> FEATURE:
<223> OTHER INFORMATION: E2f1 DNA target sequence

<400> SEQUENCE: 34
catccagctc attgccaaga a                                              21

<210> SEQ ID NO 35
<211> LENGTH: 21
<212> TYPE: DNA
<213> ORGANISM: Artificial Sequence
<220> FEATURE:
<223> OTHER INFORMATION: E2f1 DNA target sequence

<400> SEQUENCE: 35
taagagcaaa caaggcccga t                                              21

<210> SEQ ID NO 36
<211> LENGTH: 21
<212> TYPE: DNA
<213> ORGANISM: Artificial Sequence
<220> FEATURE:
<223> OTHER INFORMATION: E2f1 DNA target sequence

<400> SEQUENCE: 36
acctcttcga ctgtgacttt g                                              21

<210> SEQ ID NO 37
<211> LENGTH: 20
<212> TYPE: DNA
<213> ORGANISM: Artificial Sequence
<220> FEATURE:
<223> OTHER INFORMATION: E2f1 DNA target sequence

<400> SEQUENCE: 37
acatcaccaa cgtccttgag                                                20

<210> SEQ ID NO 38
<211> LENGTH: 21
<212> TYPE: DNA
<213> ORGANISM: Artificial Sequence
<220> FEATURE:
<223> OTHER INFORMATION: E2f1 DNA target sequence
```

```
<400> SEQUENCE: 38
ctactcagcc tggagcaaga a                                          21

<210> SEQ ID NO 39
<211> LENGTH: 21
<212> TYPE: DNA
<213> ORGANISM: Artificial Sequence
<220> FEATURE:
<223> OTHER INFORMATION: E2f1 DNA target sequence

<400> SEQUENCE: 39
caggatggat atgagatggg a                                          21

<210> SEQ ID NO 40
<211> LENGTH: 21
<212> TYPE: DNA
<213> ORGANISM: Artificial Sequence
<220> FEATURE:
<223> OTHER INFORMATION: E2f1 DNA target sequence

<400> SEQUENCE: 40
cgctatgaga cctcactgaa t                                          21

<210> SEQ ID NO 41
<211> LENGTH: 21
<212> TYPE: DNA
<213> ORGANISM: Artificial Sequence
<220> FEATURE:
<223> OTHER INFORMATION: E2f1 DNA target sequence

<400> SEQUENCE: 41
cgtggactct tcggagaact t                                          21

<210> SEQ ID NO 42
<211> LENGTH: 21
<212> TYPE: DNA
<213> ORGANISM: Artificial Sequence
<220> FEATURE:
<223> OTHER INFORMATION: E2f1 DNA target sequence

<400> SEQUENCE: 42
acctgatgaa tatctgtact a                                          21

<210> SEQ ID NO 43
<211> LENGTH: 21
<212> TYPE: DNA
<213> ORGANISM: Artificial Sequence
<220> FEATURE:
<223> OTHER INFORMATION: E2f1 DNA target sequence

<400> SEQUENCE: 43
cctgaggagt tcatcagcct t                                          21

<210> SEQ ID NO 44
<211> LENGTH: 21
<212> TYPE: DNA
<213> ORGANISM: Artificial Sequence
<220> FEATURE:
<223> OTHER INFORMATION: E2f1 DNA target sequence

<400> SEQUENCE: 44
cgctatgaga cctcactgaa t                                          21

<210> SEQ ID NO 45
<211> LENGTH: 21
```

```
<212> TYPE: DNA
<213> ORGANISM: Artificial Sequence
<220> FEATURE:
<223> OTHER INFORMATION: E2f1 DNA target sequence

<400> SEQUENCE: 45
acctgatgaa tatctgtact a                                              21

<210> SEQ ID NO 46
<211> LENGTH: 21
<212> TYPE: DNA
<213> ORGANISM: Artificial Sequence
<220> FEATURE:
<223> OTHER INFORMATION: E2f1 DNA target sequence

<400> SEQUENCE: 46
caggatggat atgagatggg a                                              21

<210> SEQ ID NO 47
<211> LENGTH: 21
<212> TYPE: DNA
<213> ORGANISM: Artificial Sequence
<220> FEATURE:
<223> OTHER INFORMATION: E2f1 DNA target sequence

<400> SEQUENCE: 47
cgtggactct tcggagaact t                                              21

<210> SEQ ID NO 48
<211> LENGTH: 21
<212> TYPE: DNA
<213> ORGANISM: Artificial Sequence
<220> FEATURE:
<223> OTHER INFORMATION: E2f1 DNA target sequence

<400> SEQUENCE: 48
acctcttcga ctgtgacttt g                                              21

<210> SEQ ID NO 49
<211> LENGTH: 21
<212> TYPE: DNA
<213> ORGANISM: Artificial Sequence
<220> FEATURE:
<223> OTHER INFORMATION: E2f2 DNA target sequence

<400> SEQUENCE: 49
ccactctata agcagggcta a                                              21

<210> SEQ ID NO 50
<211> LENGTH: 21
<212> TYPE: DNA
<213> ORGANISM: Artificial Sequence
<220> FEATURE:
<223> OTHER INFORMATION: E2f2 DNA target sequence

<400> SEQUENCE: 50
gcctatgtga cttaccagga t                                              21

<210> SEQ ID NO 51
<211> LENGTH: 21
<212> TYPE: DNA
<213> ORGANISM: Artificial Sequence
<220> FEATURE:
<223> OTHER INFORMATION: E2f2 DNA target sequence

<400> SEQUENCE: 51
```

| | | |
|---|---|---|
| gcagacagtg attgccgtca a | | 21 |

<210> SEQ ID NO 52
<211> LENGTH: 21
<212> TYPE: DNA
<213> ORGANISM: Artificial Sequence
<220> FEATURE:
<223> OTHER INFORMATION: E2f2 DNA target sequence

<400> SEQUENCE: 52

| | | |
|---|---|---|
| ccgagggcca agttgtgcga t | | 21 |

<210> SEQ ID NO 53
<211> LENGTH: 21
<212> TYPE: DNA
<213> ORGANISM: Artificial Sequence
<220> FEATURE:
<223> OTHER INFORMATION: E2f2 DNA target sequence

<400> SEQUENCE: 53

| | | |
|---|---|---|
| cagcgatctc ttcgactcct a | | 21 |

<210> SEQ ID NO 54
<211> LENGTH: 21
<212> TYPE: DNA
<213> ORGANISM: Artificial Sequence
<220> FEATURE:
<223> OTHER INFORMATION: E2f2 DNA target sequence

<400> SEQUENCE: 54

| | | |
|---|---|---|
| tccgtgctgt tggcaacttt a | | 21 |

<210> SEQ ID NO 55
<211> LENGTH: 21
<212> TYPE: DNA
<213> ORGANISM: Artificial Sequence
<220> FEATURE:
<223> OTHER INFORMATION: E2f2 DNA target sequence

<400> SEQUENCE: 55

| | | |
|---|---|---|
| gaggacaacc tgcagatata t | | 21 |

<210> SEQ ID NO 56
<211> LENGTH: 21
<212> TYPE: DNA
<213> ORGANISM: Artificial Sequence
<220> FEATURE:
<223> OTHER INFORMATION: E2f2 DNA target sequence

<400> SEQUENCE: 56

| | | |
|---|---|---|
| gtacgggtga ggagtggata a | | 21 |

<210> SEQ ID NO 57
<211> LENGTH: 21
<212> TYPE: DNA
<213> ORGANISM: Artificial Sequence
<220> FEATURE:
<223> OTHER INFORMATION: E2f3 DNA target sequence

<400> SEQUENCE: 57

| | | |
|---|---|---|
| cccgctttac tcttcaggaa t | | 21 |

<210> SEQ ID NO 58
<211> LENGTH: 21
<212> TYPE: DNA
<213> ORGANISM: Artificial Sequence

```
<220> FEATURE:
<223> OTHER INFORMATION: E2f3 DNA target sequence

<400> SEQUENCE: 58
cctcattaag aagaagtcta a                                              21

<210> SEQ ID NO 59
<211> LENGTH: 21
<212> TYPE: DNA
<213> ORGANISM: Artificial Sequence
<220> FEATURE:
<223> OTHER INFORMATION: E2f3 DNA target sequence

<400> SEQUENCE: 59
ccaaactgtt atagttgtga a                                              21

<210> SEQ ID NO 60
<211> LENGTH: 21
<212> TYPE: DNA
<213> ORGANISM: Artificial Sequence
<220> FEATURE:
<223> OTHER INFORMATION: E2f3 DNA target sequence

<400> SEQUENCE: 60
cctgactcaa tagagagcct a                                              21

<210> SEQ ID NO 61
<211> LENGTH: 21
<212> TYPE: DNA
<213> ORGANISM: Artificial Sequence
<220> FEATURE:
<223> OTHER INFORMATION: E2f3 DNA target sequence

<400> SEQUENCE: 61
ccaactcagg acatagcgat t                                              21

<210> SEQ ID NO 62
<211> LENGTH: 21
<212> TYPE: DNA
<213> ORGANISM: Artificial Sequence
<220> FEATURE:
<223> OTHER INFORMATION: E2f3 DNA target sequence

<400> SEQUENCE: 62
acgcggtatg atacgtctct t                                              21

<210> SEQ ID NO 63
<211> LENGTH: 21
<212> TYPE: DNA
<213> ORGANISM: Artificial Sequence
<220> FEATURE:
<223> OTHER INFORMATION: E2f3 DNA target sequence

<400> SEQUENCE: 63
agatcctcac cacgaacact t                                              21

<210> SEQ ID NO 64
<211> LENGTH: 21
<212> TYPE: DNA
<213> ORGANISM: Artificial Sequence
<220> FEATURE:
<223> OTHER INFORMATION: E2f3 DNA target sequence

<400> SEQUENCE: 64
gacttcatgt gtagttgatt a                                              21
```

```
<210> SEQ ID NO 65
<211> LENGTH: 21
<212> TYPE: DNA
<213> ORGANISM: Artificial Sequence
<220> FEATURE:
<223> OTHER INFORMATION: E2f3 DNA target sequence

<400> SEQUENCE: 65
acgaagtcca gatagtccaa a                                              21

<210> SEQ ID NO 66
<211> LENGTH: 21
<212> TYPE: DNA
<213> ORGANISM: Artificial Sequence
<220> FEATURE:
<223> OTHER INFORMATION: E2f3 DNA target sequence

<400> SEQUENCE: 66
ccaacctaga aggaccgttt g                                              21

<210> SEQ ID NO 67
<211> LENGTH: 21
<212> TYPE: DNA
<213> ORGANISM: Artificial Sequence
<220> FEATURE:
<223> OTHER INFORMATION: E2f3 DNA target sequence

<400> SEQUENCE: 67
gtctttgagg tctgctaata t                                              21

<210> SEQ ID NO 68
<211> LENGTH: 21
<212> TYPE: DNA
<213> ORGANISM: Artificial Sequence
<220> FEATURE:
<223> OTHER INFORMATION: H-Ras DNA target sequence

<400> SEQUENCE: 68
caagagtgcg ctgaccatcc a                                              21

<210> SEQ ID NO 69
<211> LENGTH: 21
<212> TYPE: DNA
<213> ORGANISM: Artificial Sequence
<220> FEATURE:
<223> OTHER INFORMATION: H-Ras DNA target sequence

<400> SEQUENCE: 69
agaggattcc taccggaagc a                                              21

<210> SEQ ID NO 70
<211> LENGTH: 21
<212> TYPE: DNA
<213> ORGANISM: Artificial Sequence
<220> FEATURE:
<223> OTHER INFORMATION: H-Ras DNA target sequence

<400> SEQUENCE: 70
gaggattcct accggaagca c                                              21

<210> SEQ ID NO 71
<211> LENGTH: 21
<212> TYPE: DNA
<213> ORGANISM: Artificial Sequence
<220> FEATURE:
<223> OTHER INFORMATION: H-Ras DNA target sequence
```

```
<400> SEQUENCE: 71
aagagtgcgc tgaccatcca c                                          21

<210> SEQ ID NO 72
<211> LENGTH: 21
<212> TYPE: DNA
<213> ORGANISM: Artificial Sequence
<220> FEATURE:
<223> OTHER INFORMATION: H-Ras DNA target sequence

<400> SEQUENCE: 72
gacgtgcctg ttggacatcc t                                          21

<210> SEQ ID NO 73
<211> LENGTH: 21
<212> TYPE: DNA
<213> ORGANISM: Artificial Sequence
<220> FEATURE:
<223> OTHER INFORMATION: H-Ras DNA target sequence

<400> SEQUENCE: 73
tggctgcacg cactgtggaa t                                          21

<210> SEQ ID NO 74
<211> LENGTH: 20
<212> TYPE: DNA
<213> ORGANISM: Artificial Sequence
<220> FEATURE:
<223> OTHER INFORMATION: H-Ras DNA target sequence

<400> SEQUENCE: 74
cctgttggac atcctggata                                            20

<210> SEQ ID NO 75
<211> LENGTH: 21
<212> TYPE: DNA
<213> ORGANISM: Artificial Sequence
<220> FEATURE:
<223> OTHER INFORMATION: H-Ras DNA target sequence

<400> SEQUENCE: 75
ccaggaggag tacagcgcca t                                          21

<210> SEQ ID NO 76
<211> LENGTH: 21
<212> TYPE: DNA
<213> ORGANISM: Artificial Sequence
<220> FEATURE:
<223> OTHER INFORMATION: H-Ras DNA target sequence

<400> SEQUENCE: 76
gcctgttgga catcctggat a                                          21

<210> SEQ ID NO 77
<211> LENGTH: 21
<212> TYPE: DNA
<213> ORGANISM: Artificial Sequence
<220> FEATURE:
<223> OTHER INFORMATION: H-Ras DNA target sequence

<400> SEQUENCE: 77
caagagtgcg ctgaccatcc a                                          21

<210> SEQ ID NO 78
```

```
<211> LENGTH: 21
<212> TYPE: DNA
<213> ORGANISM: Artificial Sequence
<220> FEATURE:
<223> OTHER INFORMATION: H-Ras DNA target sequence

<400> SEQUENCE: 78
agaggattcc taccggaagc a                                              21

<210> SEQ ID NO 79
<211> LENGTH: 21
<212> TYPE: DNA
<213> ORGANISM: Artificial Sequence
<220> FEATURE:
<223> OTHER INFORMATION: H-Ras DNA target sequence

<400> SEQUENCE: 79
cggaagcagg tggtcattga t                                              21

<210> SEQ ID NO 80
<211> LENGTH: 21
<212> TYPE: DNA
<213> ORGANISM: Artificial Sequence
<220> FEATURE:
<223> OTHER INFORMATION: K-ras DNA target sequence

<400> SEQUENCE: 80
cagttgagac cttctaattg g                                              21

<210> SEQ ID NO 81
<211> LENGTH: 21
<212> TYPE: DNA
<213> ORGANISM: Artificial Sequence
<220> FEATURE:
<223> OTHER INFORMATION: K-ras DNA target sequence

<400> SEQUENCE: 81
cctcgtttct acacagagaa a                                              21

<210> SEQ ID NO 82
<211> LENGTH: 21
<212> TYPE: DNA
<213> ORGANISM: Artificial Sequence
<220> FEATURE:
<223> OTHER INFORMATION: K-ras DNA target sequence

<400> SEQUENCE: 82
gatgccttct atacattagt t                                              21

<210> SEQ ID NO 83
<211> LENGTH: 21
<212> TYPE: DNA
<213> ORGANISM: Artificial Sequence
<220> FEATURE:
<223> OTHER INFORMATION: K-ras DNA target sequence

<400> SEQUENCE: 83
aggactctga agatgtacct a                                              21

<210> SEQ ID NO 84
<211> LENGTH: 21
<212> TYPE: DNA
<213> ORGANISM: Artificial Sequence
<220> FEATURE:
<223> OTHER INFORMATION: K-ras DNA target sequence

<400> SEQUENCE: 84
```
tagttggagc tggtggcgta g                                              21

<210> SEQ ID NO 85
<211> LENGTH: 21
<212> TYPE: DNA
<213> ORGANISM: Artificial Sequence
<220> FEATURE:
<223> OTHER INFORMATION: K-ras DNA target sequence

<400> SEQUENCE: 85
cctacaggaa gcaagtagta a                                              21

<210> SEQ ID NO 86
<211> LENGTH: 21
<212> TYPE: DNA
<213> ORGANISM: Artificial Sequence
<220> FEATURE:
<223> OTHER INFORMATION: N-Ras DNA target sequence

<400> SEQUENCE: 86
gaaacctgtt tgttggacat a                                              21

<210> SEQ ID NO 87
<211> LENGTH: 21
<212> TYPE: DNA
<213> ORGANISM: Artificial Sequence
<220> FEATURE:
<223> OTHER INFORMATION: N-Ras DNA target sequence

<400> SEQUENCE: 87
cagtgccatg agagaccaat a                                              21

<210> SEQ ID NO 88
<211> LENGTH: 21
<212> TYPE: DNA
<213> ORGANISM: Artificial Sequence
<220> FEATURE:
<223> OTHER INFORMATION: N-Ras DNA target sequence

<400> SEQUENCE: 88
caagagttac gggattccat t                                              21

<210> SEQ ID NO 89
<211> LENGTH: 21
<212> TYPE: DNA
<213> ORGANISM: Artificial Sequence
<220> FEATURE:
<223> OTHER INFORMATION: N-Ras DNA target sequence

<400> SEQUENCE: 89
cagtgccatg agagaccaat a                                              21

<210> SEQ ID NO 90
<211> LENGTH: 21
<212> TYPE: DNA
<213> ORGANISM: Artificial Sequence
<220> FEATURE:
<223> OTHER INFORMATION: N-Ras DNA target sequence

<400> SEQUENCE: 90
gaaacctgtt tgttggacat a                                              21

<210> SEQ ID NO 91
<211> LENGTH: 21
<212> TYPE: DNA

```
<213> ORGANISM: Artificial Sequence
<220> FEATURE:
<223> OTHER INFORMATION: N-Ras DNA target sequence

<400> SEQUENCE: 91
cgcactgaca atccagctaa t                                              21

<210> SEQ ID NO 92
<211> LENGTH: 21
<212> TYPE: DNA
<213> ORGANISM: Artificial Sequence
<220> FEATURE:
<223> OTHER INFORMATION: N-Ras DNA target sequence

<400> SEQUENCE: 92
ccatcaataa tagcaagtca t                                              21

<210> SEQ ID NO 93
<211> LENGTH: 21
<212> TYPE: RNA
<213> ORGANISM: Artificial Sequence
<220> FEATURE:
<223> OTHER INFORMATION: c-Myc RNA target sequence

<400> SEQUENCE: 93
caguugaaac acaaacuuga a                                              21

<210> SEQ ID NO 94
<211> LENGTH: 21
<212> TYPE: RNA
<213> ORGANISM: Artificial Sequence
<220> FEATURE:
<223> OTHER INFORMATION: c-Myc RNA target sequence

<400> SEQUENCE: 94
ccauaaugua aacugccuca a                                              21

<210> SEQ ID NO 95
<211> LENGTH: 21
<212> TYPE: RNA
<213> ORGANISM: Artificial Sequence
<220> FEATURE:
<223> OTHER INFORMATION: c-Myc RNA target sequence

<400> SEQUENCE: 95
caggaacuau gaccucgacu a                                              21

<210> SEQ ID NO 96
<211> LENGTH: 21
<212> TYPE: RNA
<213> ORGANISM: Artificial Sequence
<220> FEATURE:
<223> OTHER INFORMATION: c-Myc RNA target sequence

<400> SEQUENCE: 96
gcuucaccaa caggaacuau g                                              21

<210> SEQ ID NO 97
<211> LENGTH: 21
<212> TYPE: RNA
<213> ORGANISM: Artificial Sequence
<220> FEATURE:
<223> OTHER INFORMATION: c-Myc RNA target sequence

<400> SEQUENCE: 97
acugaaagau uuagccauaa u                                              21
```

```
<210> SEQ ID NO 98
<211> LENGTH: 21
<212> TYPE: RNA
<213> ORGANISM: Artificial Sequence
<220> FEATURE:
<223> OTHER INFORMATION: c-Myc RNA target sequence

<400> SEQUENCE: 98
ccagaggagg aacgagcuaa a                                              21

<210> SEQ ID NO 99
<211> LENGTH: 21
<212> TYPE: RNA
<213> ORGANISM: Artificial Sequence
<220> FEATURE:
<223> OTHER INFORMATION: c-Myc RNA target sequence

<400> SEQUENCE: 99
uacggaacuc uugugcguaa g                                              21

<210> SEQ ID NO 100
<211> LENGTH: 21
<212> TYPE: RNA
<213> ORGANISM: Artificial Sequence
<220> FEATURE:
<223> OTHER INFORMATION: c-Myc RNA target sequence

<400> SEQUENCE: 100
ccugagacag aucagcaaca a                                              21

<210> SEQ ID NO 101
<211> LENGTH: 21
<212> TYPE: RNA
<213> ORGANISM: Artificial Sequence
<220> FEATURE:
<223> OTHER INFORMATION: c-Myc RNA target sequence

<400> SEQUENCE: 101
aucaucaucc aggacuguau g                                              21

<210> SEQ ID NO 102
<211> LENGTH: 21
<212> TYPE: RNA
<213> ORGANISM: Artificial Sequence
<220> FEATURE:
<223> OTHER INFORMATION: c-Myc RNA target sequence

<400> SEQUENCE: 102
acucggugca gccguauuuc u                                              21

<210> SEQ ID NO 103
<211> LENGTH: 21
<212> TYPE: RNA
<213> ORGANISM: Artificial Sequence
<220> FEATURE:
<223> OTHER INFORMATION: L-Myc RNA target sequence

<400> SEQUENCE: 103
ccugugccac uaaacuacau u                                              21

<210> SEQ ID NO 104
<211> LENGTH: 21
<212> TYPE: RNA
<213> ORGANISM: Artificial Sequence
<220> FEATURE:
```

```
<223> OTHER INFORMATION: L-Myc RNA target sequence

<400> SEQUENCE: 104
cgaggacauc uggaagaaau u                                              21

<210> SEQ ID NO 105
<211> LENGTH: 21
<212> TYPE: RNA
<213> ORGANISM: Artificial Sequence
<220> FEATURE:
<223> OTHER INFORMATION: L-Myc RNA target sequence

<400> SEQUENCE: 105
cauuggcucu ucucaagcuc u                                              21

<210> SEQ ID NO 106
<211> LENGTH: 21
<212> TYPE: RNA
<213> ORGANISM: Artificial Sequence
<220> FEATURE:
<223> OTHER INFORMATION: L-Myc RNA target sequence

<400> SEQUENCE: 106
caggaacuac gccuccauca u                                              21

<210> SEQ ID NO 107
<211> LENGTH: 21
<212> TYPE: RNA
<213> ORGANISM: Artificial Sequence
<220> FEATURE:
<223> OTHER INFORMATION: L-Myc RNA target sequence

<400> SEQUENCE: 107
cccaagcgac ucgguaagg a                                               21

<210> SEQ ID NO 108
<211> LENGTH: 21
<212> TYPE: RNA
<213> ORGANISM: Artificial Sequence
<220> FEATURE:
<223> OTHER INFORMATION: L-Myc RNA target sequence

<400> SEQUENCE: 108
uggcgcuuag agaggacaau a                                              21

<210> SEQ ID NO 109
<211> LENGTH: 21
<212> TYPE: RNA
<213> ORGANISM: Artificial Sequence
<220> FEATURE:
<223> OTHER INFORMATION: L-Myc RNA target sequence

<400> SEQUENCE: 109
uguugguaaa caguuuggaa a                                              21

<210> SEQ ID NO 110
<211> LENGTH: 21
<212> TYPE: RNA
<213> ORGANISM: Artificial Sequence
<220> FEATURE:
<223> OTHER INFORMATION: L-Myc RNA target sequence

<400> SEQUENCE: 110
ucuccaguug gcuuuacuuu a                                              21
```

```
<210> SEQ ID NO 111
<211> LENGTH: 21
<212> TYPE: RNA
<213> ORGANISM: Artificial Sequence
<220> FEATURE:
<223> OTHER INFORMATION: L-Myc RNA target sequence

<400> SEQUENCE: 111
gaggcuuaga gauagacaau c                                             21

<210> SEQ ID NO 112
<211> LENGTH: 21
<212> TYPE: RNA
<213> ORGANISM: Artificial Sequence
<220> FEATURE:
<223> OTHER INFORMATION: N-Myc RNA target sequence

<400> SEQUENCE: 112
cagcagcagu ugcuaaagaa a                                             21

<210> SEQ ID NO 113
<211> LENGTH: 21
<212> TYPE: RNA
<213> ORGANISM: Artificial Sequence
<220> FEATURE:
<223> OTHER INFORMATION: N-Myc RNA target sequence

<400> SEQUENCE: 113
gcgucgcaga aaccacaaca u                                             21

<210> SEQ ID NO 114
<211> LENGTH: 21
<212> TYPE: RNA
<213> ORGANISM: Artificial Sequence
<220> FEATURE:
<223> OTHER INFORMATION: N-Myc RNA target sequence

<400> SEQUENCE: 114
cugagcgauu cagaugauga a                                             21

<210> SEQ ID NO 115
<211> LENGTH: 21
<212> TYPE: RNA
<213> ORGANISM: Artificial Sequence
<220> FEATURE:
<223> OTHER INFORMATION: N-Myc RNA target sequence

<400> SEQUENCE: 115
gccaguauua gacuggaagu u                                             21

<210> SEQ ID NO 116
<211> LENGTH: 21
<212> TYPE: RNA
<213> ORGANISM: Artificial Sequence
<220> FEATURE:
<223> OTHER INFORMATION: N-Myc RNA target sequence

<400> SEQUENCE: 116
cggacgaaga ugacuucuac u                                             21

<210> SEQ ID NO 117
<211> LENGTH: 21
<212> TYPE: RNA
<213> ORGANISM: Artificial Sequence
<220> FEATURE:
<223> OTHER INFORMATION: N-Myc RNA target sequence
```

```
<400> SEQUENCE: 117
caccuccaug acagcgcuaa a                                              21

<210> SEQ ID NO 118
<211> LENGTH: 21
<212> TYPE: RNA
<213> ORGANISM: Artificial Sequence
<220> FEATURE:
<223> OTHER INFORMATION: N-Myc RNA target sequence

<400> SEQUENCE: 118
cuucuacccg gacgaagaug a                                              21

<210> SEQ ID NO 119
<211> LENGTH: 21
<212> TYPE: RNA
<213> ORGANISM: Artificial Sequence
<220> FEATURE:
<223> OTHER INFORMATION: N-Myc RNA target sequence

<400> SEQUENCE: 119
agacagcagc aguugcuaaa g                                              21

<210> SEQ ID NO 120
<211> LENGTH: 21
<212> TYPE: RNA
<213> ORGANISM: Artificial Sequence
<220> FEATURE:
<223> OTHER INFORMATION: N-Myc RNA target sequence

<400> SEQUENCE: 120
cauaccuaag uacuguaaua a                                              21

<210> SEQ ID NO 121
<211> LENGTH: 21
<212> TYPE: RNA
<213> ORGANISM: Artificial Sequence
<220> FEATURE:
<223> OTHER INFORMATION: N-Myc RNA target sequence

<400> SEQUENCE: 121
ucggacuugc uagacgcuuc u                                              21

<210> SEQ ID NO 122
<211> LENGTH: 21
<212> TYPE: RNA
<213> ORGANISM: Artificial Sequence
<220> FEATURE:
<223> OTHER INFORMATION: N-Myc RNA target sequence

<400> SEQUENCE: 122
acguccgcuc aagaguguca u                                              21

<210> SEQ ID NO 123
<211> LENGTH: 21
<212> TYPE: RNA
<213> ORGANISM: Artificial Sequence
<220> FEATURE:
<223> OTHER INFORMATION: N-Myc RNA target sequence

<400> SEQUENCE: 123
cacggagaug cugcuugaga a                                              21

<210> SEQ ID NO 124
<211> LENGTH: 21
```

```
<212> TYPE: RNA
<213> ORGANISM: Artificial Sequence
<220> FEATURE:
<223> OTHER INFORMATION: N-Myc RNA target sequence

<400> SEQUENCE: 124
acgugccgga guugguaaag a                                              21

<210> SEQ ID NO 125
<211> LENGTH: 21
<212> TYPE: RNA
<213> ORGANISM: Artificial Sequence
<220> FEATURE:
<223> OTHER INFORMATION: E2f1 RNA target sequence

<400> SEQUENCE: 125
uaacugcacu uucggcccuu u                                              21

<210> SEQ ID NO 126
<211> LENGTH: 21
<212> TYPE: RNA
<213> ORGANISM: Artificial Sequence
<220> FEATURE:
<223> OTHER INFORMATION: E2f1 RNA target sequence

<400> SEQUENCE: 126
cauccagcuc auugccaaga a                                              21

<210> SEQ ID NO 127
<211> LENGTH: 21
<212> TYPE: RNA
<213> ORGANISM: Artificial Sequence
<220> FEATURE:
<223> OTHER INFORMATION: E2f1 RNA target sequence

<400> SEQUENCE: 127
uaagagcaaa caaggcccga u                                              21

<210> SEQ ID NO 128
<211> LENGTH: 21
<212> TYPE: RNA
<213> ORGANISM: Artificial Sequence
<220> FEATURE:
<223> OTHER INFORMATION: E2f1 RNA target sequence

<400> SEQUENCE: 128
accucuucga cugugacuuu g                                              21

<210> SEQ ID NO 129
<211> LENGTH: 20
<212> TYPE: RNA
<213> ORGANISM: Artificial Sequence
<220> FEATURE:
<223> OTHER INFORMATION: E2f1 RNA target sequence

<400> SEQUENCE: 129
acaucaccaa cguccuugag                                                20

<210> SEQ ID NO 130
<211> LENGTH: 21
<212> TYPE: RNA
<213> ORGANISM: Artificial Sequence
<220> FEATURE:
<223> OTHER INFORMATION: E2f1 RNA target sequence

<400> SEQUENCE: 130
```
cuacucagcc uggagcaaga a     21

<210> SEQ ID NO 131
<211> LENGTH: 21
<212> TYPE: RNA
<213> ORGANISM: Artificial Sequence
<220> FEATURE:
<223> OTHER INFORMATION: E2f1 RNA target sequence

<400> SEQUENCE: 131
caggauggau augagauggg a     21

<210> SEQ ID NO 132
<211> LENGTH: 21
<212> TYPE: RNA
<213> ORGANISM: Artificial Sequence
<220> FEATURE:
<223> OTHER INFORMATION: E2f1 RNA target sequence

<400> SEQUENCE: 132
cgcuaugaga ccucacugaa u     21

<210> SEQ ID NO 133
<211> LENGTH: 21
<212> TYPE: RNA
<213> ORGANISM: Artificial Sequence
<220> FEATURE:
<223> OTHER INFORMATION: E2f1 RNA target sequence

<400> SEQUENCE: 133
cguggacucu ucggagaacu u     21

<210> SEQ ID NO 134
<211> LENGTH: 21
<212> TYPE: RNA
<213> ORGANISM: Artificial Sequence
<220> FEATURE:
<223> OTHER INFORMATION: E2f1 RNA target sequence

<400> SEQUENCE: 134
accugaugaa uaucuguacu a     21

<210> SEQ ID NO 135
<211> LENGTH: 21
<212> TYPE: RNA
<213> ORGANISM: Artificial Sequence
<220> FEATURE:
<223> OTHER INFORMATION: E2f1 RNA target sequence

<400> SEQUENCE: 135
ccugaggagu ucaucagccu u     21

<210> SEQ ID NO 136
<211> LENGTH: 21
<212> TYPE: RNA
<213> ORGANISM: Artificial Sequence
<220> FEATURE:
<223> OTHER INFORMATION: E2f1 RNA target sequence

<400> SEQUENCE: 136
cgcuaugaga ccucacugaa u     21

<210> SEQ ID NO 137
<211> LENGTH: 21
<212> TYPE: RNA
<213> ORGANISM: Artificial Sequence

```
<220> FEATURE:
<223> OTHER INFORMATION: E2f1 RNA target sequence

<400> SEQUENCE: 137
accugaugaa uaucuguacu a                                              21

<210> SEQ ID NO 138
<211> LENGTH: 21
<212> TYPE: RNA
<213> ORGANISM: Artificial Sequence
<220> FEATURE:
<223> OTHER INFORMATION: E2f1 RNA target sequence

<400> SEQUENCE: 138
caggauggau augagauggg a                                              21

<210> SEQ ID NO 139
<211> LENGTH: 21
<212> TYPE: RNA
<213> ORGANISM: Artificial Sequence
<220> FEATURE:
<223> OTHER INFORMATION: E2f1 RNA target sequence

<400> SEQUENCE: 139
cguggacucu ucggagaacu u                                              21

<210> SEQ ID NO 140
<211> LENGTH: 21
<212> TYPE: RNA
<213> ORGANISM: Artificial Sequence
<220> FEATURE:
<223> OTHER INFORMATION: E2f1 RNA target sequence

<400> SEQUENCE: 140
accucuucga cugugacuuu g                                              21

<210> SEQ ID NO 141
<211> LENGTH: 21
<212> TYPE: RNA
<213> ORGANISM: Artificial Sequence
<220> FEATURE:
<223> OTHER INFORMATION: E2f2 RNA target sequence

<400> SEQUENCE: 141
ccacucuaua agcagggcua a                                              21

<210> SEQ ID NO 142
<211> LENGTH: 21
<212> TYPE: RNA
<213> ORGANISM: Artificial Sequence
<220> FEATURE:
<223> OTHER INFORMATION: E2f2 RNA target sequence

<400> SEQUENCE: 142
gccuauguga cuuaccagga u                                              21

<210> SEQ ID NO 143
<211> LENGTH: 21
<212> TYPE: RNA
<213> ORGANISM: Artificial Sequence
<220> FEATURE:
<223> OTHER INFORMATION: E2f2 RNA target sequence

<400> SEQUENCE: 143
gcagacagug auugccguca a                                              21
```

```
<210> SEQ ID NO 144
<211> LENGTH: 21
<212> TYPE: RNA
<213> ORGANISM: Artificial Sequence
<220> FEATURE:
<223> OTHER INFORMATION: E2f2 RNA target sequence

<400> SEQUENCE: 144
ccgagggcca aguugugcga u                                           21

<210> SEQ ID NO 145
<211> LENGTH: 21
<212> TYPE: RNA
<213> ORGANISM: Artificial Sequence
<220> FEATURE:
<223> OTHER INFORMATION: E2f2 RNA target sequence

<400> SEQUENCE: 145
cagcgaucuc uucgacuccu a                                           21

<210> SEQ ID NO 146
<211> LENGTH: 21
<212> TYPE: RNA
<213> ORGANISM: Artificial Sequence
<220> FEATURE:
<223> OTHER INFORMATION: E2f2 RNA target sequence

<400> SEQUENCE: 146
uccgugcugu uggcaacuuu a                                           21

<210> SEQ ID NO 147
<211> LENGTH: 21
<212> TYPE: RNA
<213> ORGANISM: Artificial Sequence
<220> FEATURE:
<223> OTHER INFORMATION: E2f2 RNA target sequence

<400> SEQUENCE: 147
gaggacaacc ugcagauaua u                                           21

<210> SEQ ID NO 148
<211> LENGTH: 21
<212> TYPE: RNA
<213> ORGANISM: Artificial Sequence
<220> FEATURE:
<223> OTHER INFORMATION: E2f2 RNA target sequence

<400> SEQUENCE: 148
guacggguga ggaguggaua a                                           21

<210> SEQ ID NO 149
<211> LENGTH: 21
<212> TYPE: RNA
<213> ORGANISM: Artificial Sequence
<220> FEATURE:
<223> OTHER INFORMATION: E2f3 RNA target sequence

<400> SEQUENCE: 149
cccgcuuuac ucuucaggaa u                                           21

<210> SEQ ID NO 150
<211> LENGTH: 21
<212> TYPE: RNA
<213> ORGANISM: Artificial Sequence
<220> FEATURE:
<223> OTHER INFORMATION: E2f3 RNA target sequence
```

```
<400> SEQUENCE: 150
ccucauuaag aagaagucua a                                              21

<210> SEQ ID NO 151
<211> LENGTH: 21
<212> TYPE: RNA
<213> ORGANISM: Artificial Sequence
<220> FEATURE:
<223> OTHER INFORMATION: E2f3 RNA target sequence

<400> SEQUENCE: 151
ccaaacuguu auaguuguga a                                              21

<210> SEQ ID NO 152
<211> LENGTH: 21
<212> TYPE: RNA
<213> ORGANISM: Artificial Sequence
<220> FEATURE:
<223> OTHER INFORMATION: E2f3 RNA target sequence

<400> SEQUENCE: 152
ccugacucaa uagagagccu a                                              21

<210> SEQ ID NO 153
<211> LENGTH: 21
<212> TYPE: RNA
<213> ORGANISM: Artificial Sequence
<220> FEATURE:
<223> OTHER INFORMATION: E2f3 RNA target sequence

<400> SEQUENCE: 153
ccaacucagg acauagcgau u                                              21

<210> SEQ ID NO 154
<211> LENGTH: 21
<212> TYPE: RNA
<213> ORGANISM: Artificial Sequence
<220> FEATURE:
<223> OTHER INFORMATION: E2f3 RNA target sequence

<400> SEQUENCE: 154
acgcgguaug auacgucucu u                                              21

<210> SEQ ID NO 155
<211> LENGTH: 21
<212> TYPE: RNA
<213> ORGANISM: Artificial Sequence
<220> FEATURE:
<223> OTHER INFORMATION: E2f3 RNA target sequence

<400> SEQUENCE: 155
agauccucac cacgaacacu u                                              21

<210> SEQ ID NO 156
<211> LENGTH: 21
<212> TYPE: RNA
<213> ORGANISM: Artificial Sequence
<220> FEATURE:
<223> OTHER INFORMATION: E2f3 RNA target sequence

<400> SEQUENCE: 156
gacuucaugu guaguugauu a                                              21

<210> SEQ ID NO 157
```

```
<211> LENGTH: 21
<212> TYPE: RNA
<213> ORGANISM: Artificial Sequence
<220> FEATURE:
<223> OTHER INFORMATION: E2f3 RNA target sequence

<400> SEQUENCE: 157
acgaagucca gauaguccaa a                                              21

<210> SEQ ID NO 158
<211> LENGTH: 21
<212> TYPE: RNA
<213> ORGANISM: Artificial Sequence
<220> FEATURE:
<223> OTHER INFORMATION: E2f3 RNA target sequence

<400> SEQUENCE: 158
ccaaccuaga aggaccguuu g                                              21

<210> SEQ ID NO 159
<211> LENGTH: 21
<212> TYPE: RNA
<213> ORGANISM: Artificial Sequence
<220> FEATURE:
<223> OTHER INFORMATION: E2f3 RNA target sequence

<400> SEQUENCE: 159
gucuuugagg ucugcuaaua u                                              21

<210> SEQ ID NO 160
<211> LENGTH: 21
<212> TYPE: RNA
<213> ORGANISM: Artificial Sequence
<220> FEATURE:
<223> OTHER INFORMATION: H-Ras RNA target sequence

<400> SEQUENCE: 160
caagagugcg cugaccaucc a                                              21

<210> SEQ ID NO 161
<211> LENGTH: 21
<212> TYPE: RNA
<213> ORGANISM: Artificial Sequence
<220> FEATURE:
<223> OTHER INFORMATION: H-Ras RNA target sequence

<400> SEQUENCE: 161
agaggauucc uaccggaagc a                                              21

<210> SEQ ID NO 162
<211> LENGTH: 21
<212> TYPE: RNA
<213> ORGANISM: Artificial Sequence
<220> FEATURE:
<223> OTHER INFORMATION: H-Ras RNA target sequence

<400> SEQUENCE: 162
gaggauuccu accggaagca c                                              21

<210> SEQ ID NO 163
<211> LENGTH: 21
<212> TYPE: RNA
<213> ORGANISM: Artificial Sequence
<220> FEATURE:
<223> OTHER INFORMATION: H-Ras RNA target sequence

<400> SEQUENCE: 163
```

-continued

```
aagagugcgc ugaccaucca c                                         21

<210> SEQ ID NO 164
<211> LENGTH: 21
<212> TYPE: RNA
<213> ORGANISM: Artificial Sequence
<220> FEATURE:
<223> OTHER INFORMATION: H-Ras RNA target sequence

<400> SEQUENCE: 164
gacgugccug uuggacaucc u                                         21

<210> SEQ ID NO 165
<211> LENGTH: 21
<212> TYPE: RNA
<213> ORGANISM: Artificial Sequence
<220> FEATURE:
<223> OTHER INFORMATION: H-Ras RNA target sequence

<400> SEQUENCE: 165
uggcugcacg cacuguggaa u                                         21

<210> SEQ ID NO 166
<211> LENGTH: 20
<212> TYPE: RNA
<213> ORGANISM: Artificial Sequence
<220> FEATURE:
<223> OTHER INFORMATION: H-Ras RNA target sequence

<400> SEQUENCE: 166
ccuguuggac auccuggaua                                           20

<210> SEQ ID NO 167
<211> LENGTH: 21
<212> TYPE: RNA
<213> ORGANISM: Artificial Sequence
<220> FEATURE:
<223> OTHER INFORMATION: H-Ras RNA target sequence

<400> SEQUENCE: 167
ccaggaggag uacagcgcca u                                         21

<210> SEQ ID NO 168
<211> LENGTH: 21
<212> TYPE: RNA
<213> ORGANISM: Artificial Sequence
<220> FEATURE:
<223> OTHER INFORMATION: H-Ras RNA target sequence

<400> SEQUENCE: 168
gccuguugga cauccuggau a                                         21

<210> SEQ ID NO 169
<211> LENGTH: 21
<212> TYPE: RNA
<213> ORGANISM: Artificial Sequence
<220> FEATURE:
<223> OTHER INFORMATION: H-Ras RNA target sequence

<400> SEQUENCE: 169
caagagugcg cugaccaucc a                                         21

<210> SEQ ID NO 170
<211> LENGTH: 21
<212> TYPE: RNA
```

<213> ORGANISM: Artificial Sequence
<220> FEATURE:
<223> OTHER INFORMATION: H-Ras RNA target sequence

<400> SEQUENCE: 170
agaggauucc uaccggaagc a                                              21

<210> SEQ ID NO 171
<211> LENGTH: 21
<212> TYPE: RNA
<213> ORGANISM: Artificial Sequence
<220> FEATURE:
<223> OTHER INFORMATION: H-Ras RNA target sequence

<400> SEQUENCE: 171
cggaagcagg uggucauuga u                                              21

<210> SEQ ID NO 172
<211> LENGTH: 21
<212> TYPE: RNA
<213> ORGANISM: Artificial Sequence
<220> FEATURE:
<223> OTHER INFORMATION: K-ras RNA target sequence

<400> SEQUENCE: 172
caguugagac cuucuaauug g                                              21

<210> SEQ ID NO 173
<211> LENGTH: 21
<212> TYPE: RNA
<213> ORGANISM: Artificial Sequence
<220> FEATURE:
<223> OTHER INFORMATION: K-ras RNA target sequence

<400> SEQUENCE: 173
ccucguuucu acacagagaa a                                              21

<210> SEQ ID NO 174
<211> LENGTH: 21
<212> TYPE: RNA
<213> ORGANISM: Artificial Sequence
<220> FEATURE:
<223> OTHER INFORMATION: K-ras RNA target sequence

<400> SEQUENCE: 174
gaugccuucu auacauuagu u                                              21

<210> SEQ ID NO 175
<211> LENGTH: 21
<212> TYPE: RNA
<213> ORGANISM: Artificial Sequence
<220> FEATURE:
<223> OTHER INFORMATION: K-ras RNA target sequence

<400> SEQUENCE: 175
aggacucuga agauguaccu a                                              21

<210> SEQ ID NO 176
<211> LENGTH: 21
<212> TYPE: RNA
<213> ORGANISM: Artificial Sequence
<220> FEATURE:
<223> OTHER INFORMATION: K-ras RNA target sequence

<400> SEQUENCE: 176
uaguuggagc ugguggcgua g                                              21

<210> SEQ ID NO 177
<211> LENGTH: 21
<212> TYPE: RNA
<213> ORGANISM: Artificial Sequence
<220> FEATURE:
<223> OTHER INFORMATION: K-ras RNA target sequence

<400> SEQUENCE: 177
ccuacaggaa gcaaguagua a                                              21

<210> SEQ ID NO 178
<211> LENGTH: 21
<212> TYPE: RNA
<213> ORGANISM: Artificial Sequence
<220> FEATURE:
<223> OTHER INFORMATION: N-Ras RNA target sequence

<400> SEQUENCE: 178
gaaaccuguu uguuggacau a                                              21

<210> SEQ ID NO 179
<211> LENGTH: 21
<212> TYPE: RNA
<213> ORGANISM: Artificial Sequence
<220> FEATURE:
<223> OTHER INFORMATION: N-Ras RNA target sequence

<400> SEQUENCE: 179
cagugccaug agagaccaau a                                              21

<210> SEQ ID NO 180
<211> LENGTH: 21
<212> TYPE: RNA
<213> ORGANISM: Artificial Sequence
<220> FEATURE:
<223> OTHER INFORMATION: N-Ras RNA target sequence

<400> SEQUENCE: 180
caagaguuac gggauuccau u                                              21

<210> SEQ ID NO 181
<211> LENGTH: 21
<212> TYPE: RNA
<213> ORGANISM: Artificial Sequence
<220> FEATURE:
<223> OTHER INFORMATION: N-Ras RNA target sequence

<400> SEQUENCE: 181
cagugccaug agagaccaau a                                              21

<210> SEQ ID NO 182
<211> LENGTH: 21
<212> TYPE: RNA
<213> ORGANISM: Artificial Sequence
<220> FEATURE:
<223> OTHER INFORMATION: N-Ras RNA target sequence

<400> SEQUENCE: 182
gaaaccuguu uguuggacau a                                              21

<210> SEQ ID NO 183
<211> LENGTH: 21
<212> TYPE: RNA
<213> ORGANISM: Artificial Sequence
<220> FEATURE:

<223> OTHER INFORMATION: N-Ras RNA target sequence

<400> SEQUENCE: 183
cgcacugaca auccagcuaa u                                                    21

<210> SEQ ID NO 184
<211> LENGTH: 21
<212> TYPE: RNA
<213> ORGANISM: Artificial Sequence
<220> FEATURE:
<223> OTHER INFORMATION: N-Ras RNA target sequence

<400> SEQUENCE: 184
ccaucaauaa uagcaaguca u                                                    21

<210> SEQ ID NO 185
<211> LENGTH: 58
<212> TYPE: DNA
<213> ORGANISM: Artificial Sequence
<220> FEATURE:
<223> OTHER INFORMATION: c-Myc commercial DNA sequence encoding shRNA
      against cMyc (Sigma)

<400> SEQUENCE: 185
ccggcagttg aaacacaaac ttgaactcga gttcaagttt gtgtttcaac tgtttttg           58

<210> SEQ ID NO 186
<211> LENGTH: 58
<212> TYPE: DNA
<213> ORGANISM: Artificial Sequence
<220> FEATURE:
<223> OTHER INFORMATION: c-Myc commercial DNA sequence encoding shRNA
      against cMyc (Sigma)

<400> SEQUENCE: 186
ccggcctgag acagatcagc aacaactcga gttgttgctg atctgtctca ggtttttg           58

<210> SEQ ID NO 187
<211> LENGTH: 58
<212> TYPE: DNA
<213> ORGANISM: Artificial Sequence
<220> FEATURE:
<223> OTHER INFORMATION: c-Myc commercial DNA sequence encoding shRNA
      against cMyc (Sigma)

<400> SEQUENCE: 187
ccggcctgag acagatcagc aacaactcga gttgttgctg atctgtctca ggtttttg           58

<210> SEQ ID NO 188
<211> LENGTH: 58
<212> TYPE: DNA
<213> ORGANISM: Artificial Sequence
<220> FEATURE:
<223> OTHER INFORMATION: c-Myc commercial DNA sequence encoding shRNA
      against cMyc (Sigma)

<400> SEQUENCE: 188
ccggccataa tgtaaactgc ctcaactcga gttgaggcag tttacattat ggtttttg           58

<210> SEQ ID NO 189
<211> LENGTH: 58
<212> TYPE: DNA
<213> ORGANISM: Artificial Sequence
<220> FEATURE:
<223> OTHER INFORMATION: c-Myc commercial DNA sequence encoding shRNA
      against cMyc (Sigma)

-continued

<400> SEQUENCE: 189
ccggcaggaa ctatgacctc gactactcga gtagtcgagg tcatagttcc tgtttttg    58

<210> SEQ ID NO 190
<211> LENGTH: 58
<212> TYPE: DNA
<213> ORGANISM: Artificial Sequence
<220> FEATURE:
<223> OTHER INFORMATION: c-Myc commercial DNA sequence encoding shRNA
      against cMyc (Sigma)

<400> SEQUENCE: 190
ccgggcttca ccaacaggaa ctatgctcga gcatagttcc tgttggtgaa gcttttttg    58

<210> SEQ ID NO 191
<211> LENGTH: 58
<212> TYPE: DNA
<213> ORGANISM: Artificial Sequence
<220> FEATURE:
<223> OTHER INFORMATION: c-Myc commercial DNA sequence encoding shRNA
      against cMyc (Sigma)

<400> SEQUENCE: 191
ccggactgaa agatttagcc ataatctcga gattatggct aaatctttca gtttttg    58

<210> SEQ ID NO 192
<211> LENGTH: 58
<212> TYPE: DNA
<213> ORGANISM: Artificial Sequence
<220> FEATURE:
<223> OTHER INFORMATION: c-Myc commercial DNA sequence encoding shRNA
      against cMyc (Sigma)

<400> SEQUENCE: 192
ccggccagag gaggaacgag ctaaactcga gtttagctcg ttcctcctct ggtttttg    58

<210> SEQ ID NO 193
<211> LENGTH: 58
<212> TYPE: DNA
<213> ORGANISM: Artificial Sequence
<220> FEATURE:
<223> OTHER INFORMATION: c-Myc commercial DNA sequence encoding shRNA
      against cMyc (Sigma)

<400> SEQUENCE: 193
ccggtacgga actcttgtgc gtaagctcga gcttacgcac aagagttccg tatttttg    58

<210> SEQ ID NO 194
<211> LENGTH: 58
<212> TYPE: DNA
<213> ORGANISM: Artificial Sequence
<220> FEATURE:
<223> OTHER INFORMATION: c-Myc commercial DNA sequence encoding shRNA
      against cMyc (Sigma)

<400> SEQUENCE: 194
ccggcctgag acagatcagc aacaactcga gttgttgctg atctgtctca ggtttttg    58

<210> SEQ ID NO 195
<211> LENGTH: 58
<212> TYPE: DNA
<213> ORGANISM: Artificial Sequence
<220> FEATURE:
<223> OTHER INFORMATION: c-Myc commercial DNA sequence encoding shRNA
      against cMyc (Sigma)

<400> SEQUENCE: 195
ccggatcatc atccaggact gtatgctcga gcatacagtc ctggatgatg attttttg    58

<210> SEQ ID NO 196
<211> LENGTH: 58
<212> TYPE: DNA
<213> ORGANISM: Artificial Sequence
<220> FEATURE:
<223> OTHER INFORMATION: c-Myc commercial DNA sequence encoding shRNA
      against cMyc (Sigma)

<400> SEQUENCE: 196
ccggactcgg tgcagccgta tttctctcga gagaaatacg gctgcaccga gtttttg    58

<210> SEQ ID NO 197
<211> LENGTH: 57
<212> TYPE: DNA
<213> ORGANISM: Artificial Sequence
<220> FEATURE:
<223> OTHER INFORMATION: L-Myc commercial DNA sequence encoding shRNA
      against L-Myc (Sigma)

<400> SEQUENCE: 197
ccggcctgtg ccactaaact acattctcga gaatgtagtt tagtggcaca ggttttt    57

<210> SEQ ID NO 198
<211> LENGTH: 57
<212> TYPE: DNA
<213> ORGANISM: Artificial Sequence
<220> FEATURE:
<223> OTHER INFORMATION: L-Myc commercial DNA sequence encoding shRNA
      against L-Myc (Sigma)

<400> SEQUENCE: 198
ccggcgagga catctggaag aaattctcga gaatttcttc cagatgtcct cgttttt    57

<210> SEQ ID NO 199
<211> LENGTH: 57
<212> TYPE: DNA
<213> ORGANISM: Artificial Sequence
<220> FEATURE:
<223> OTHER INFORMATION: L-Myc commercial DNA sequence encoding shRNA
      against L-Myc (Sigma)

<400> SEQUENCE: 199
ccggcattgg ctcttctcaa gctctctcga gagagcttga aagagccaa tgttttt    57

<210> SEQ ID NO 200
<211> LENGTH: 57
<212> TYPE: DNA
<213> ORGANISM: Artificial Sequence
<220> FEATURE:
<223> OTHER INFORMATION: L-Myc commercial DNA sequence encoding shRNA
      against L-Myc (Sigma)

<400> SEQUENCE: 200
ccggcaggaa ctacgcctcc atcatctcga gatgatggag gcgtagttcc tgttttt    57

<210> SEQ ID NO 201
<211> LENGTH: 57
<212> TYPE: DNA
<213> ORGANISM: Artificial Sequence
<220> FEATURE:
<223> OTHER INFORMATION: L-Myc commercial DNA sequence encoding shRNA
      against L-Myc (Sigma)

<400> SEQUENCE: 201
ccggcccaag cgactcgggt aaggactcga gtccttaccc gagtcgcttg ggttttt    57

<210> SEQ ID NO 202
<211> LENGTH: 59
<212> TYPE: DNA
<213> ORGANISM: Artificial Sequence
<220> FEATURE:
<223> OTHER INFORMATION: L-Myc commercial DNA sequence encoding shRNA
      against L-Myc (Sigma)

<400> SEQUENCE: 202
ccggtggcgc ttagagagga caatactcga gtattgtcct ctctaagcgc catttttg    59

<210> SEQ ID NO 203
<211> LENGTH: 59
<212> TYPE: DNA
<213> ORGANISM: Artificial Sequence
<220> FEATURE:
<223> OTHER INFORMATION: L-Myc commercial DNA sequence encoding shRNA
      against L-Myc (Sigma)

<400> SEQUENCE: 203
ccggtgttgg taaacagttt ggaaactcga gtttccaaac tgtttaccaa catttttg    59

<210> SEQ ID NO 204
<211> LENGTH: 59
<212> TYPE: DNA
<213> ORGANISM: Artificial Sequence
<220> FEATURE:
<223> OTHER INFORMATION: L-Myc commercial DNA sequence encoding shRNA
      against L-Myc (Sigma)

<400> SEQUENCE: 204
ccggtctcca gttggcttta ctttactcga gtaaagtaaa gccaactgga gatttttg    59

<210> SEQ ID NO 205
<211> LENGTH: 59
<212> TYPE: DNA
<213> ORGANISM: Artificial Sequence
<220> FEATURE:
<223> OTHER INFORMATION: L-Myc commercial DNA sequence encoding shRNA
      against L-Myc (Sigma)

<400> SEQUENCE: 205
ccgggaggct tagagataga caatcctcga ggattgtcta tctctaagcc tcttttttg    59

<210> SEQ ID NO 206
<211> LENGTH: 57
<212> TYPE: DNA
<213> ORGANISM: Artificial Sequence
<220> FEATURE:
<223> OTHER INFORMATION: N-Myc commercial DNA sequence encoding shRNA
      against N-Myc (Sigma)

<400> SEQUENCE: 206
ccggcagcag cagttgctaa agaaactcga gtttctttag caactgctgc tgttttt    57

<210> SEQ ID NO 207
<211> LENGTH: 57
<212> TYPE: DNA
<213> ORGANISM: Artificial Sequence
<220> FEATURE:
<223> OTHER INFORMATION: N-Myc commercial DNA sequence encoding shRNA
      against N-Myc (Sigma)

<400> SEQUENCE: 207
ccgggcgtcg cagaaaccac aacatctcga gatgttgtgg tttctgcgac gctttt    57

<210> SEQ ID NO 208
<211> LENGTH: 57
<212> TYPE: DNA
<213> ORGANISM: Artificial Sequence
<220> FEATURE:
<223> OTHER INFORMATION: N-Myc commercial DNA sequence encoding shRNA
      against N-Myc (Sigma)

<400> SEQUENCE: 208
ccggctgagc gattcagatg atgaactcga gttcatcatc tgaatcgctc agttttt         57

<210> SEQ ID NO 209
<211> LENGTH: 57
<212> TYPE: DNA
<213> ORGANISM: Artificial Sequence
<220> FEATURE:
<223> OTHER INFORMATION: N-Myc commercial DNA sequence encoding shRNA
      against N-Myc (Sigma)

<400> SEQUENCE: 209
ccgggccagt attagactgg aagttctcga gaacttccag tctaatactg gctttt          57

<210> SEQ ID NO 210
<211> LENGTH: 57
<212> TYPE: DNA
<213> ORGANISM: Artificial Sequence
<220> FEATURE:
<223> OTHER INFORMATION: N-Myc commercial DNA sequence encoding shRNA
      against N-Myc (Sigma)

<400> SEQUENCE: 210
ccggcggacg aagatgactt ctactctcga gagtagaagt catcttcgtc cgttttt         57

<210> SEQ ID NO 211
<211> LENGTH: 58
<212> TYPE: DNA
<213> ORGANISM: Artificial Sequence
<220> FEATURE:
<223> OTHER INFORMATION: N-Myc commercial DNA sequence encoding shRNA
      against N-Myc (Sigma)

<400> SEQUENCE: 211
ccggcacctc catgacagcg ctaaactcga gtttagcgct gtcatggagg tgttttg         58

<210> SEQ ID NO 212
<211> LENGTH: 58
<212> TYPE: DNA
<213> ORGANISM: Artificial Sequence
<220> FEATURE:
<223> OTHER INFORMATION: N-Myc commercial DNA sequence encoding shRNA
      against N-Myc (Sigma)

<400> SEQUENCE: 212
ccggcttcta cccggacgaa gatgactcga gtcatcttcg tccgggtaga agttttg         58

<210> SEQ ID NO 213
<211> LENGTH: 58
<212> TYPE: DNA
<213> ORGANISM: Artificial Sequence
<220> FEATURE:
<223> OTHER INFORMATION: N-Myc commercial DNA sequence encoding shRNA
      against N-Myc (Sigma)

<400> SEQUENCE: 213
ccggagacag cagcagttgc taaagctcga gctttagcaa ctgctgctgt ctttttg         58

```
<210> SEQ ID NO 214
<211> LENGTH: 58
<212> TYPE: DNA
<213> ORGANISM: Artificial Sequence
<220> FEATURE:
<223> OTHER INFORMATION: N-Myc commercial DNA sequence encoding shRNA
      against N-Myc (Sigma)

<400> SEQUENCE: 214
ccggcatacc taagtactgt aataactcga gttattacag tacttaggta tgtttttg          58

<210> SEQ ID NO 215
<211> LENGTH: 59
<212> TYPE: DNA
<213> ORGANISM: Artificial Sequence
<220> FEATURE:
<223> OTHER INFORMATION: N-Myc commercial DNA sequence encoding shRNA
      against N-Myc (Sigma)

<400> SEQUENCE: 215
ccggtcggac ttgctagacg cttctctcga gagaagcgtc tagcaagtcc gatttttg         59

<210> SEQ ID NO 216
<211> LENGTH: 59
<212> TYPE: DNA
<213> ORGANISM: Artificial Sequence
<220> FEATURE:
<223> OTHER INFORMATION: N-Myc commercial DNA sequence encoding shRNA
      against N-Myc (Sigma)

<400> SEQUENCE: 216
ccggacgtcc gctcaagagt gtcatctcga gatgacactc ttgagcggac gttttttg         59

<210> SEQ ID NO 217
<211> LENGTH: 59
<212> TYPE: DNA
<213> ORGANISM: Artificial Sequence
<220> FEATURE:
<223> OTHER INFORMATION: N-Myc commercial DNA sequence encoding shRNA
      against N-Myc (Sigma)

<400> SEQUENCE: 217
ccggcacgga gatgctgctt gagaactcga gttctcaagc agcatctccg tgtttttg         59

<210> SEQ ID NO 218
<211> LENGTH: 59
<212> TYPE: DNA
<213> ORGANISM: Artificial Sequence
<220> FEATURE:
<223> OTHER INFORMATION: N-Myc commercial DNA sequence encoding shRNA
      against N-Myc (Sigma)

<400> SEQUENCE: 218
ccggacgtgc cggagttggt aaagactcga gtctttacca actccggcac gttttttg         59
```